US008722850B2

(12) United States Patent
Vescovi et al.

(10) Patent No.: US 8,722,850 B2
(45) Date of Patent: May 13, 2014

(54) SELF-ASSEMBLING PEPTIDES AND THEIR USE IN THE FORMATION OF HYDROGELS

(75) Inventors: Angelo Luigi Vescovi, Maroggia (CH); Fabrizio Gelain, Corsico (IT)

(73) Assignee: Universita' Degli Studi di Milano Bicocca, Milan (IT)

( * ) Notice: Subject to any disclaimer, the term of this patent is extended or adjusted under 35 U.S.C. 154(b) by 0 days.

(21) Appl. No.: 13/642,081

(22) PCT Filed: Apr. 19, 2011

(86) PCT No.: PCT/EP2011/056237
§ 371 (c)(1),
(2), (4) Date: Oct. 18, 2012

(87) PCT Pub. No.: WO2011/131671
PCT Pub. Date: Oct. 27, 2011

(65) Prior Publication Data
US 2013/0053324 A1     Feb. 28, 2013

(30) Foreign Application Priority Data

Apr. 19, 2010   (WO) .................. PCT/IB2010/051700

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07F 7/00* | (2006.01) |
| *C07K 14/00* | (2006.01) |
| *C12N 5/00* | (2006.01) |
| *C12N 5/07* | (2010.01) |
| *C12N 5/071* | (2010.01) |
| *C12N 5/073* | (2010.01) |
| *C12N 5/077* | (2010.01) |
| *C12N 5/0775* | (2010.01) |

(52) U.S. Cl.
USPC ............ 530/300; 530/324; 530/350; 524/35; 435/373; 435/383; 435/395; 435/396; 435/397; 435/398; 435/401; 435/402

(58) Field of Classification Search
None
See application file for complete search history.

(56) References Cited

U.S. PATENT DOCUMENTS

| | | | |
|---|---|---|---|
| 6,548,630 B1 | 4/2003 | Zhang et al. | |
| 7,371,719 B2 | 5/2008 | Stupp et al. | |
| 8,022,178 B2 * | 9/2011 | Horii et al. | .............. 530/324 |
| 2009/0162437 A1 | 6/2009 | Horii et al. | |

FOREIGN PATENT DOCUMENTS

WO       2008/039483       4/2008

OTHER PUBLICATIONS

Tibbitt, M.W. & Anseth, K.S. "Hydrogels as Extracellular Matrix Mimics for 3D Cell Culture" Biotechnology and Bioengineering, vol. 103, No. 4, (Jul. 1, 2009) pp. 655-663.
Hamidi, M. et al., "Hydrogel nanoparticles in drug delivery" Advanced Drug Delivery Reviews 60, (2008), pp. 1638-1649.
Nisbet, D.R. et al., "Neural Tissue Engineering of the CNS Using Hydrogels" Journal of Biomedical Materials Research Part B: Applied Biomaterials 87B, (2007) pp. 251-263.
Kisiday, J. et al. "Self-assembling peptide hydrogel fosters chondrocyte extracellular matrix production and cell division: Implications for cartilage tissue repair" Proc Natl Acad Sci (PNAS) vol. 99, No. 15., (Jul. 23, 2002) pp. 9996-10001.
Gelain, F. et al., "Designer Self-Assembling Peptide Nanofiber Scaffolds for Adult Mouse Neural Stem Cell 3-Dimensional Cultures" PLoS ONE, Issue 1, e119 (Dec. 2006) pp. 1-11.
Zhang, S. et al., "Designer self-assembling peptide nanofiber scaffolds for 3D tissue cell cultures" Seminars in Cancer Biology 15 (2005) pp. 413-420.
Zhang, S. et al., "Spontaneous assembly of a self-complementary oligopeptide to form a stable macroscopic membrane" Proc. Natl. Acad. Sci. USA vol. 90 (Apr. 1993) pp. 3334-3338.
Gazit, E. "Self-assembled peptide nanostructures: the design of molecular building blocks and their technological utilization" Chem. Soc. Rev. 36, (2007) pp. 1263-1269.
Taraballi, F. et al. "Effect of functionalization on the self-assembling propensity of β-sheet forming peptides" Soft Matter 5, (2009) pp. 660-668.
Jitrapakdee, S. & Wallace, J.C. "The Biotin Enzyme Family: Conserved Structural Motifs and Domain Rearrangements" Current Protein and Peptide Science vol. 4, No. 3 (2003) pp. 217-229.
Lei, Y. et al.,"Theoretical Study of Cooperativity in Biotin" J. Phys. Chem. B vol. 111, No. 51 (2007) pp. 14370-14377.
Zuckermann, R.N. & Kodadek, T. "Peptoids as potential therapeutics" Current Opinion in Molecular Therapeutics vol. 11, No. 3 (2009) pp. 299-307.

(Continued)

*Primary Examiner* — Chang-Yu Wang
(74) *Attorney, Agent, or Firm* — Stradley Ronon Stevens & Young, LLP

(57) ABSTRACT

There is described a group of novel self-assembling peptides (SAPs), comprising biotinylated and unbiotinylated sequences, hybrid peptide-peptoid sequences, branched sequences for a total of 48 tested motifs, showing a heterogeneous ensemble of spontaneously self-assembled structures at the nano- and microscale, ranging from short tabular fibers to twisted ribbons, nanotubes and hierarchical self-assembled micrometer-long sheets. Specifically, the SAPs according to the present invention which initially spontaneous assemble, surprisingly form stable solid scaffolds upon exposure to neutral pH buffer. Further these SAPs allow adhesion, proliferation and differentiation of murine and human neural stem cells and have self-healing propensity. They also did not exert toxic effects in the central nervous system, can stop bleeding and foster nervous regeneration. Therefore, the SAPs according to the present invention are improved biomaterials, a highly valid and useful alternative which may replace the known SAPs, thus overcoming the disadvantages related thereto.

15 Claims, 26 Drawing Sheets

(56) References Cited

OTHER PUBLICATIONS

D'Souza, S.E. et al., "Arginyl-glycyl-aspartic acid (RGD): a cell adhesion motif" TIBS 16 (Jul. 1991) pp. 246-250.

Reches, M. & Gazit, E. "Casting Metal Nanowires Within Discrete Self-Assembled Peptide Nanotubes" Science vol. 300 (Apr. 25, 2003) pp. 625-627.

Vescovi, A.L., et al. "bFGF Regulates the Proliferative Fate of Unipotent (Neuronal) and Bipotent (Neuronal/Astroglial) EGF-Generated CNS Progenitor Cells" Neuron vol. 11 (Nov. 1993) pp. 951-966.

Vescovi, A.L. et al. "Isolation and Cloning of Multipotential Stem Cells from the Embryonic Human CNS and Establishment of Transplantable Human Neural Stem Cell Lines by Epigenetic Stimulation" Experimental Neurology 156, (1999) pp. 71-83.

International Search Report and Written Opinion as mailed Oct. 13, 2011 by the European Patent Office in its capacity as Internatinal Search Authority for corresponding international PCT application No. PCT/EP2011/056237.

Gelain, F. et al., "BMHP1-Derived Self-Assembling Peptides: Hierarchically Assembled Structures with Self-Healing Propensity and Potential for Tissue Engineering Applications" ACS NANO vol. 5, No. 3, (2011) pp. 1845-1859.

Hucknall, Angus M. Thesis "A Self-Assembling Peptide Scaffold Functionalized for Use with Neural Stem Cells" Massachusetts Institute of Technology, Dept. of Materials Science and Engineering (Jul. 22, 2005) pp. 1-35.

Di Fonzo, et al., "Hierarchically organized nanostructured TiO2 for photocatalysis applications", Nanotechnology, vol. 20, No. 1, 2009, pp. 1-7.

* cited by examiner

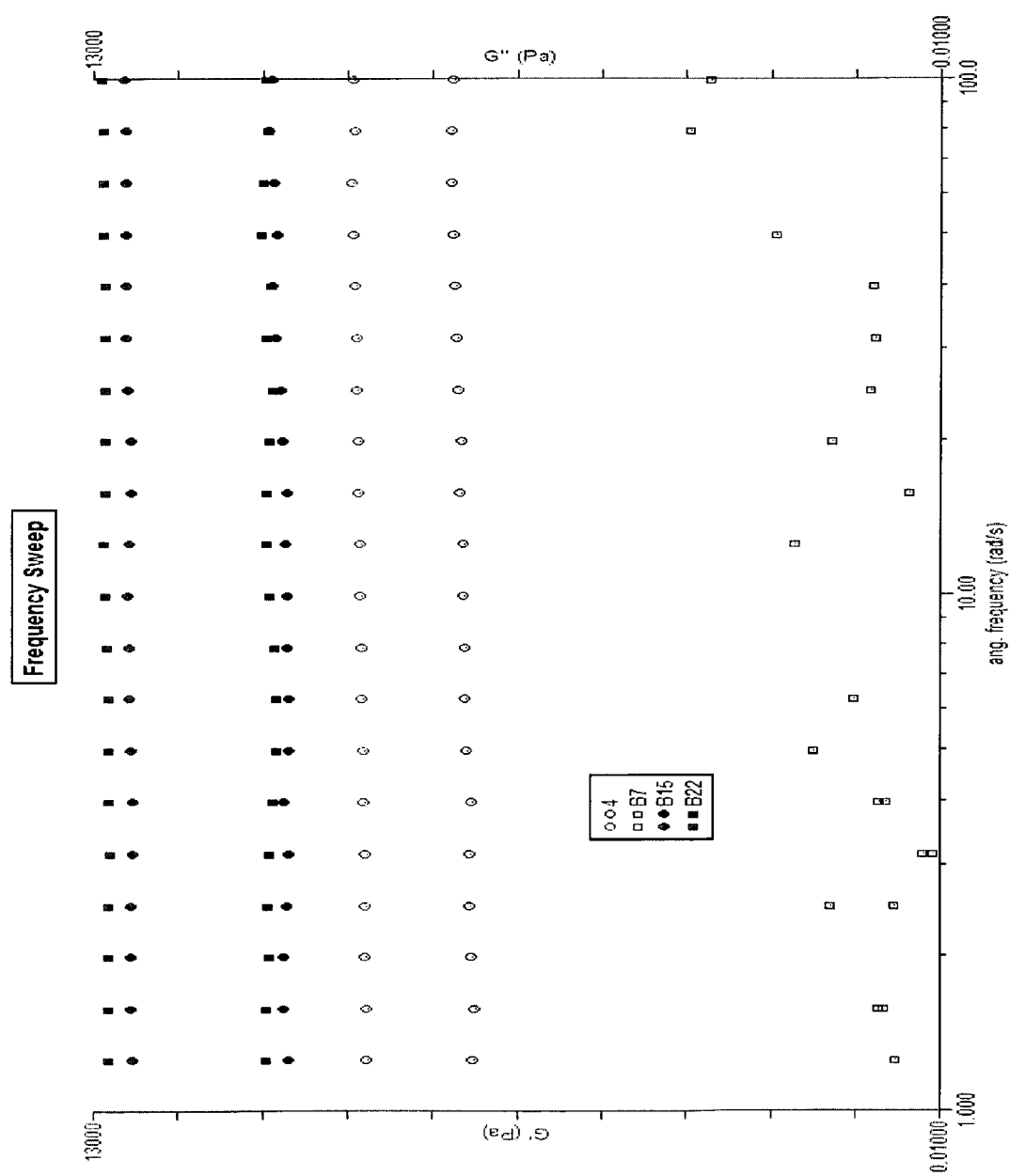

Figure 2 d

| Peptide identification numbers | Peptide sequences | G' pre-assembling | G' post-assembling |
|---|---|---|---|
| B3 * (SEQ ID NO. 1) | Biot-GGGPFSSTKT-CONH2 | 67 Pa | 2917 Pa |
| 4 " (SEQ ID NO. 2) | Ac-WGGGPFSSTKT-CONH2 | 0.05 Pa | 158 Pa |
| B10 (SEQ ID NO. 3) | Biot-GGGPFSSTDT-CONH2 | Immediate Gelation | Immediate Gelation |
| B11 (SEQ ID NO.4) | Biot-GGGPFSSTNT-CONH2 | Immediate Gelation | Immediate Gelation |
| B12 (SEQ ID NO.5) | Biot-GGGPFSSTET-CONH2 | Immediate Gelation | Immediate Gelation |
| B13 (SEQ ID NO. 6) | Biot-GGGPFSSTQT-CONH2 | Immediate Gelation | Immediate Gelation |
| B15 (SEQ ID NO. 7) | Biot-GGGAFSSTKT-CONH2 | 18 Pa | 8500 Pa |
| B17 (SEQ ID NO. 8) | Biot-GGGPFSETKT-CONH2 | 2.12 Pa | 1615 Pa |
| B19 ** (SEQ ID NO.9) | Biot-GGGAFSSTKTGRGD-CONH2 | 0.144 Pa | 114.7 Pa |
| B22 * (SEQ ID NO. 10) | Biot-GGGPFSSTRT-CONH2 | 58.68 Pa | 8715 Pa |
| B24 * (SEQ ID NO. 11) | Biot-GGGAFASTKT-CONH2 | 2.72 Pa | 6502 Pa |
| B25 (SEQ ID NO. 12) | Biot-GGGGGPFSSTKT-CONH2 | 3.08 Pa | 403.5 Pa |
| B27 " (SEQ ID NO.13) | Biot-GGGPWSSTKT-CONH2 | 22.3 Pa | 8566 |
| B28 ^ (SEQ ID NO.14) | Biot-GGG(Propylamine)FSSTKT-CONH2 | 0.2628 Pa | 687.2 Pa |
| 30 "** (SEQ ID NO.15) | Ac-WGGGAFASTKT-CONH2 | 0.55 Pa | 101 Pa |
| 31 ** (SEQ ID NO.16) | Ac-WGGGAFSSTKT-CONH2 | 4.02 Pa | 5337 Pa |
| 1 (SEQ ID NO.22) | Ac-PFSSTKT-CONH2 | N.G. | No Gelation |
| 2 (SEQ ID NO.23) | Ac-GGGPFSSTKT-CONH2 | <0.001 Pa | No Gelation |

| B64 | Biot-GGGKFSSTPT-CONH2 |
| B65 | Biot-GGGPKSSTFT-CONH2 |
| B66 | Biot-GGGPFSSKTT-CONH2 |
| B67 | Biot-GGGPFSSTTK-CONH2 |

| B32 | Biot-GGGAWASTKT-CONH2 | B15 | Biot-GGGAFSSTKT-CONH2 |
| B33 | Biot-GGGAFASTKA-CONH2 | B24 | Biot-GGGAFASTKT-CONH2 |
| B40 | Biot-GGGAASSTKT-CONH2 | B54 | Biot-GGGAFASTKTGIKVAV-CONH2 |
| B41 | Biot-GGGAFAATKT-CONH2 | B58 | (Biot-GGG)2KFSSTKT-CONH2 |
| B42 | Biot-GGGAFASAKA-CONH2 | 59 | Ac-FGGGAFASTKTGIKVAV-CONH2 |
| | | B44 | Biot-GGGAFAAAKA-CONH2 |
| | | 61 | Ac-FGGGAFSSTKT-CONH2 |

| 4 | Ac-WGGGPFSSTKT-CONH2 |
|---|---|
| 37 | Ac-FGGGPFSSTKT-CONH2 |
| 60 | Ac-YGGGPFSSTKT-CONH2 |

B10 Biot-GGGPFSSTDT-CONH2
B11 Biot-GGGPFSSTNT-CONH2
B12 Biot-GGGPFSSTET-CONH2
B13 Biot-GGGPFSSTQT-CONH2
B43 Biot-GGGPFSSTAT-CONH2

| | |
|---|---|
| B53 | Biot-GGGPFSSTKTGIKVAV-CONH2 |
| B50 | Biot-GAFASTKT-CONH2 |
| B18 | Biot-GGGPFSSTKTGRGD-CONH2 |
| B19 | Biot-GGGAFSSTKTGRGD-CONH2 |
| B25 | Biot-GGGGGPFSSTKT-CONH2 |
| B28 | Biot-GGG(Propylamine)FSSTKT-CONH2 |
| B29 | Biot-GPFSSTKT-CONH2 |
| 30 | Ac-WGGGAFASTKT-CONH2 |
| 31 | Ac-WGGGAFSSTKT-CONH2 |
| B45 | Biot-GGGPFSSAKT-CONH2 |
| B52 | Biot-GGGAFASTKTGRGD-CONH2 |
| B51 | Biot-GGGGGAFASTKT-CONH2 |

B3  Biot-GGGPFSSTKT-CONH2
B17 Biot-GGGPFSETKT-CONH2
B22 Biot-GGGPFSSTRT-CONH2
B27 Biot-GGGPWSSTKT-CONH2
B34 Biot-GGGPFSSTKTP-CONH2
B39 Biot-GGGPYSSTKTP-CONH2
B46 Biot-GGGPFSATKT-CONH2
B47 Biot-GGGPFSCTKT-CONH2
B48 Biot-GGGPFCSTKT-CONH2
B57 Biot-GGGAFAK-CONH2

| Diffraction maxima of the tested peptides | | | | | |
|---|---|---|---|---|---|
| Peptide | d, Å | intensity | Peptide | d, Å | intensity |
| B3 | 21.00 | s | B25 | 19.60 | w |
|  | 9.00 | m |  | 12.00 | w |
|  | 7.10 | m |  | 8.00 | vw |
|  | 5.20 | w |  | 6.60 | vw |
|  | 4.60 | vs |  | 4.60 | vs |
|  | 3.70 | w |  | 3.80 | m |
|  | 3.20 | w |  | 3.00 | w |
|  | 2.70 | w |  | 2.40 | w |
|  | 2.30 | vw | B33 | 16.90 | w |
| 4 | 23.50 | s |  | 8.50 | vw |
|  | 11.70 | w |  | 6.50 | vw |
|  | 4.60 | s |  | 4.60 | vs |
|  | 3.80 | w |  | 4.00 | w |
|  | 2.38 | vw |  | 3.70 | m |
| B12 | 20.50 | m |  | 2.90 | vw |
|  | 9.50 | w |  | 2.40 | vw |
|  | 7.00 | w | B34 | 21.0 | m |
|  | 4.60 | vs |  | 7.10 | w |
|  | 4.30 | vs |  | 5.30 | w |
|  | 3.81 | m |  | 4.60 | vs |
|  | 2.34 | vw |  | 3.70 | w |
| B13 | 21.90 | s | B47 | 21.50 | m |
|  | 17.30 | s |  | 17.10 | m |
|  | 12.00 | w |  | 9.10 | w |
|  | 10.10 | w |  | 7.10 | m |
|  | 8.70 | w |  | 4.60 | vs |
|  | 7.10 | m |  | 4.30 | s |
|  | 5.09 | w |  | 3.70 | w |
|  | 4.60 | vs |  | 3.20 | vw |
|  | 3.60 | m |  | 2.80 | vw |
|  | 3.20 | w |  | 2.50 | vw |
|  | 2.70 | w |  | 2.30 | vw |
|  | 2.30 | vw | B48 | 17.50 | vw |
| B15 | 17.30 | m |  | 5.50 | vw |
|  | 7.70 | w |  | 4.60 | s |
|  | 4.60 | vs |  | 4.00 | m |
|  | 4.16 | w |  | 3.70 | vw |
|  | 3.70 | m |  | 2.30 | vw |
|  | 3.40 | vw | B53 | 20.82 | vw |
|  | 2.30 | vw |  | 9.7 | w |
| B19 | 28.60 | m |  | 7.50 | w |
|  | 8.10 | w |  | 4.60 | vs |
|  | 4.64 | vs |  | 3.70 | m |
|  | 4.08 | m |  | 3.10 | vw |
|  | 3.85 | w |  | 2.80 | vw |
|  | 2.40 | vw |  | 2.30 | vw | vs, very strong; s, strong; m, medium; w, weak; vw, very weak

Figure 4 c

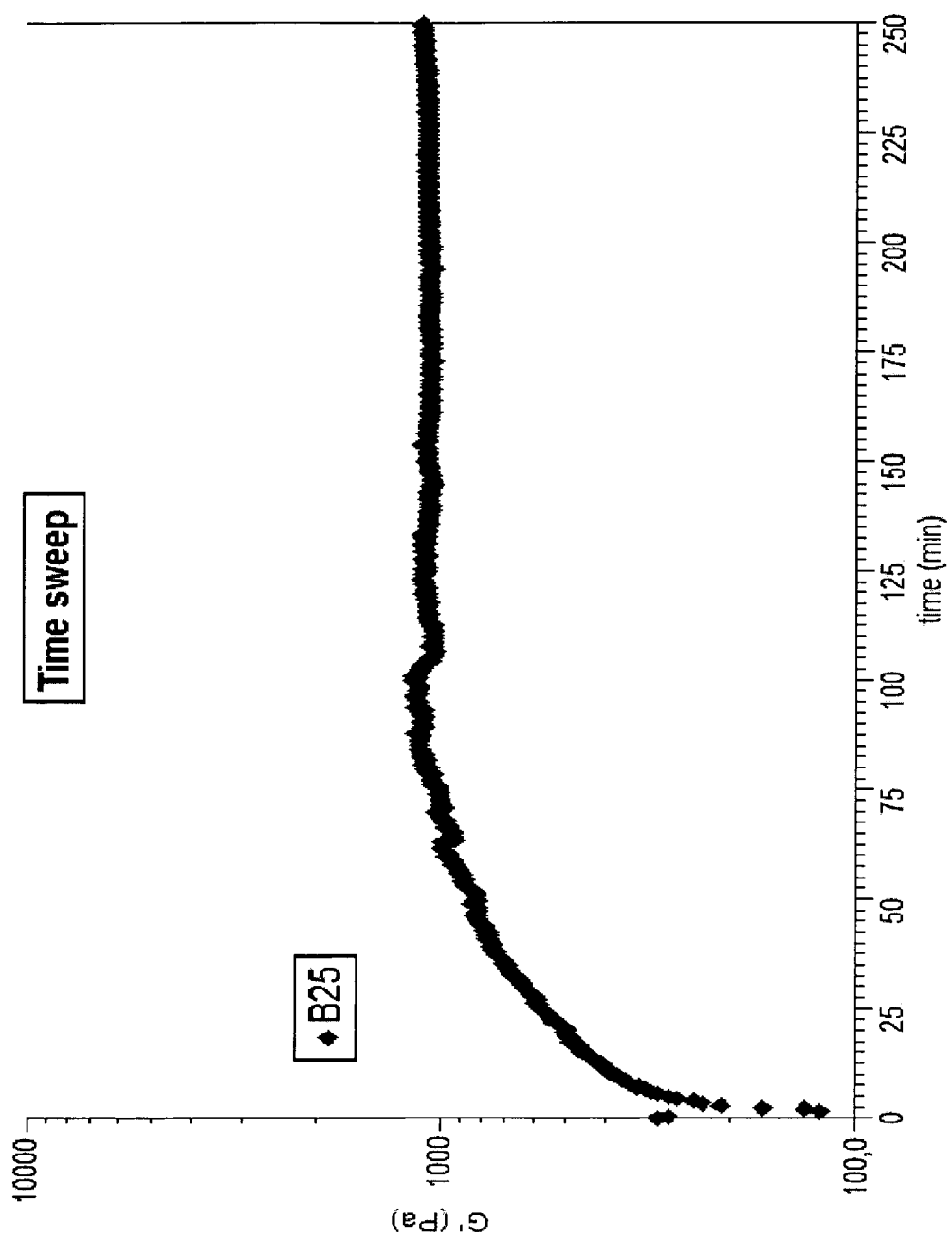

SELF-ASSEMBLING PEPTIDES AND THEIR USE IN THE FORMATION OF HYDROGELS

CROSS REFERENCE TO RELATED APPLICATIONS

This application is the U.S. national phase of and claims priority to International Application Number PCT/EP2011/056237 filed on Apr. 19, 2011 which claims priority to International Application Number PCT/IB2010/051700 filed Apr. 19, 2010, the contents of each of which are herein incorporated by reference in their entireties.

FIELD OF THE INVENTION

The present invention concerns the field of synthetic hydrogels. This polymeric class of materials has a wide range of applications in the biomedical field, in electrochemical biosensing, in self-assembling circuits and transistors for computers and in material sciences due to its high versatility.

REFERENCE TO A SEQUENCE LISTING

This application includes a Sequence Listing submitted electronically as a text file named 10303PTUS_01_SEQLST-TEXT, created on Apr. 19, 2011, with a size of 10,000 bytes. The Sequence Listing is incorporated by reference herein.

STATE OF THE ART

Hydrogels, mainly ascribable to soft materials, have a wide range of applications in 3-D cell culturing, drug delivery and tissue engineering (1-3). There are numerous examples of synthetic or natural polymer-based hydrogels.

Natural derived polymers, including agarose, collagen, fibrin, chitosan, and hyaluronic acid, can form hydrogels. Despite their origin, natural components have several disadvantages, such as the tendency to induce inflammatory response and pathogen transfer due to undefined factors that cannot be eliminated by purification prior to implantation, the significant degree of variability between different lots and the difficulty of availability of large scale sources, particularly if human proteins are involved.

Synthetic polymers can be of two types, those made of small low molecular weight peptides and those made of large monomers such as poly (ethylene glycol), polyacrylamide, poly (vinyl alcohol). This second class of synthetic polymers can form hydrogels under suitable conditions. However, regardless of their purity of chemical tailorability such synthetic hydrogels made of large monomers have several disadvantages such as: biocompatibility, biodegradation products and host responses upon transplantation. Moreover functionalization with bioactive motifs (from 3 to 8-mer peptides), necessary to obtain the desired cellular response, has can be achieved with usually harsh reactions available only for a limited number of short peptides.

Research related to low molecular weight self-assembling peptides which can form hydrogels, synthetic but naturally inspired, has been rapidly expanding in the recent years.

Construction of self-assembling small molecular hydrogels has received considerable attention due to their potential as nanostructured materials amenable of easy functionalization and capable of creating microenvironments suited for culturing cells, triggering tissue regeneration and other applications beyond life-sciences such as electrochemical sensing, molecular electronics and construction of three-dimensional nanoscale systems.

Peptide-based scaffolds are interesting candidates for hydrogelation because they can be self-assembled in mild solvent conditions via formation of various non-covalent interactions in water, including hydrogen-bonding, electrostatic, or π-π interactions. These interactions, eventually, lead to the formation of organized supramolecular assemblies that can give rise to nanofibers, nanotubes and nanoparticles (7, 8).

The need is therefore increasingly felt for novel synthetic peptides belonging to the promising class of self-assembling peptides for the development of solid scaffolds, which are synthetic but naturally inspired: both precious qualities that allow for is molecular design, safe usage in clinics and reasonable scale up production in clinics. Further, such novel polymers need to overcome the disadvantages described above.

Up to now, the majority of known self-assembling short peptides which form synthetic hydrogels are N-terminally protected.

Few examples of hydrogels formed from self-assembling, water-soluble, synthetic short oligopeptides having no protecting group have been described: among them the most important class comprises peptides of alternating hydrophilic and hydrophobic amino acid residues such as described in U.S. Pat. No. 7,371,719 and in U.S. Pat. No. 6,548,630 (7).

In fact, US20090162437 provides self-assembling peptides with a first amino acid domain which mediates self-assembly, comprising alternating hydrophobic and hydrophilic amino acids that self-assemble into a macroscopic structure when present in unmodified form; and a second amino acid domain that does not mediate self-assembly in isolated form, wherein the second amino acid domain comprises at least one minimal biologically active sequence.

Several functional motifs have been attached to self-assembling peptides. It is known that that the functional motif, BMHP, a member of the class of bone marrow homing peptides has the following sequence PFSSTKT (SEQ ID NO. 48), and can foster neural stem cell adhesion and differentiation (5). BMPH can stabilize the β-sheet structures (10) found in the self-assembling peptide RADA16-I nanofibers, when linked, via a glycine-spacer, to the RADA16-I self-assembling "core". Nonetheless most of the known self-assembling peptides feature poor mechanical properties, giving very soft and fragile scaffolds when assembled. Therefore, it is the object of the present invention to find improved SAPs which overcome the disadvantages related to known SAPs and may replace them.

SUMMARY OF THE INVENTION

The present invention concerns the self-assembling peptide (SAP) which consists of an amino acid domain, having from 7 to 17 aminoacids, said domain being:

```
                                    SEQ ID N. 1
        -GGGPFSSTKT-

SEQ ID N. 2
        -WGGGPFSSTKT-

SEQ ID N. 3
        -GGGPFSSTDT-
```

-GGGPFSSTNT- SEQ ID N. 4
-GGGPFSSTET- SEQ ID N. 5
-GGGPFSSTQT- SEQ ID N. 6
-GGGAFSSTKT- SEQ ID N. 7
-GGGPFSETKT- SEQ ID N. 8
-GGGAFSSTKTGRGD- SEQ ID N. 9
-GGGPFSSTRT- SEQ ID N. 10
-GGGAFASTKT- SEQ ID N. 11
-GGGGGPFSSTKT- SEQ ID N. 12
-GGGPWSSTKT- SEQ ID N. 13
-GGG(Propylamine)FSSTKT- SEQ ID N. 14
-WGGGAFASTKT- SEQ ID N. 15
-WGGGAFSSTKT- SEQ ID N. 16
-GGGKFSSTPT- SEQ ID N. 17
-GGGPKSSTFT- SEQ ID N. 18
-GGGPFSSKTT- SEQ ID N. 19
-GGGPFSSTTK- SEQ ID N. 20
-GGGGPFSSTKT- SEQ ID N. 21
-GGGPFSSTKTGRGD- SEQ ID N. 22
-GPFSSTKT- SEQ ID N. 23
-GGGAWASTKT- SEQ ID N. 24
-GGGAFASTKA- SEQ ID N. 25
-GGGPFSSTKTP SEQ ID N. 26
-FGGGPFSSTKT- SEQ ID N. 27
-GGGPYSSTKT- SEQ ID N. 28
-GGGAASSTKT- SEQ ID N. 29
-GGGAFAATKT- SEQ ID N. 30
-GGGAFASAKA- SEQ ID N. 31
-GGGPFSSTAT- SEQ ID N. 32
-GGGAFAAAKA- SEQ ID N. 33
-GGGPFSSAKT- SEQ ID N. 34
-GGGPFSATKT- SEQ ID N. 35
-GGGPFSCTKT- SEQ ID N. 36
-GGGPFCSTKT- SEQ ID N. 37
-GAFASTKT- SEQ ID N. 38
-GGGGGAFASTKT- SEQ ID N. 39
-GGGAFASTKTGRGD- SEQ ID N. 40
-GGGPFSSTKTGIKVAV- SEQ ID N. 41
-GGGAFASTKTGIKVAV- SEQ ID N. 42
-GGGAFAK- SEQ ID N. 43
-(GGG)$_2$-KFSSTKT- SEQ ID N. 44
-FGGGAFASTKTGIKVAV- SEQ ID N. 45
-YGGGPFSSTKT-; SEQ ID N. 46
or
-FGGGAFSSTKT-. SEQ ID N. 47

The present invention therefore concerns a novel group of self-assembling peptides (SAPs), wherein the SAPs consist of novel peptides, which are optionally biotinylated and unbiotinylated sequences at the N-termini and amidated or not at the C-termini, hybrid peptide-peptoid sequences, for a total of 47 tested motifs. The SAPs having a sequence from SEQ ID NO 1 to SEQ ID NO 47 are all linear peptides, with the exception of SEQ ID NO.44 which is a branched peptide with two identical GGG branches.

For the purposes of the present invention, each peptide has a peptide identification number and a corresponding SEQ ID NO., as indicated in the following detailed description.

The present invention further describes a hydrogel comprising the self-assembling peptides and a hydrogelating ingredient.

A further aspect of the present invention is a self-assembling peptide polymer comprising at least 2 identical self-assembling peptides.

A still further aspect of the present invention is a self-assembling peptide polymer comprising at least 2 different self-assembling peptides.

A still further aspect is the use of the self-assembling peptide polymer of the invention as a medicament.

The present invention further describes a tabular nanofiber comprising at least 2 is identical self-assembling peptides.

The present invention still further describes a tabular nanofiber comprising at least 2 different self-assembling peptides.

A further aspect of the present invention is a complex interwoven membrane made of at least 2 tabular nanofibres.

A still further aspect of the invention is a self-assembled nanostructure consisting of 2 or more identical peptides of the invention.

A still further aspect of the invention is a self-assembled nanostructure consisting of 2 or more different peptides of the invention.

A still further aspect of the invention is a pharmaceutical composition comprising at least one polymer and a pharmaceutically bioactive excipient.

BRIEF DESCRIPTION OF THE DRAWINGS

The characteristics and advantages of the present invention will be apparent from the detailed description reported below, from the Examples given for illustrative and non-limiting purposes, and from the annexed Figures, wherein.

* Peptide dissolved and tested at 1%;
"peptide tested 7 days after dissolution;
**peptide dissolved and tested at 3%;
^peptide dissolved and tested at 2%.

Figure 3:
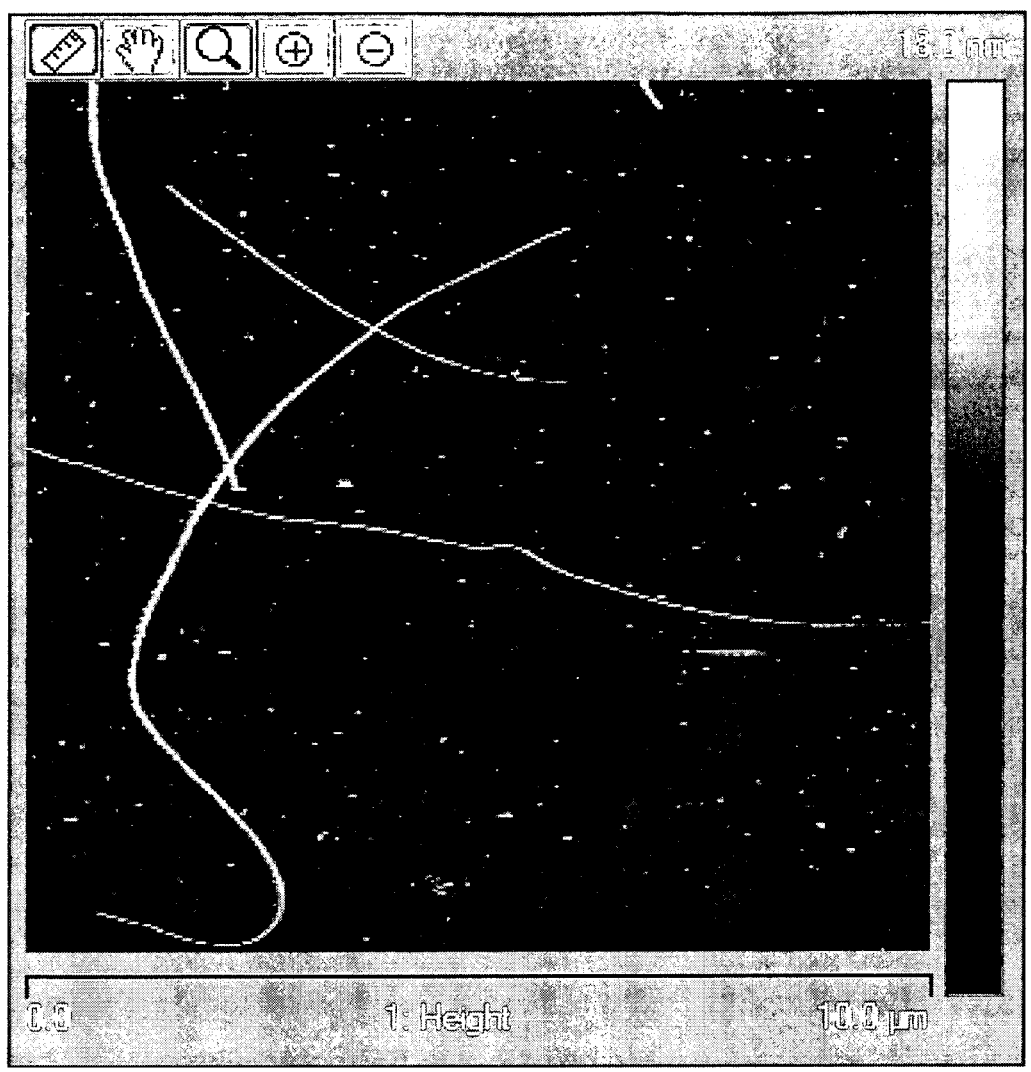
Figure 3:
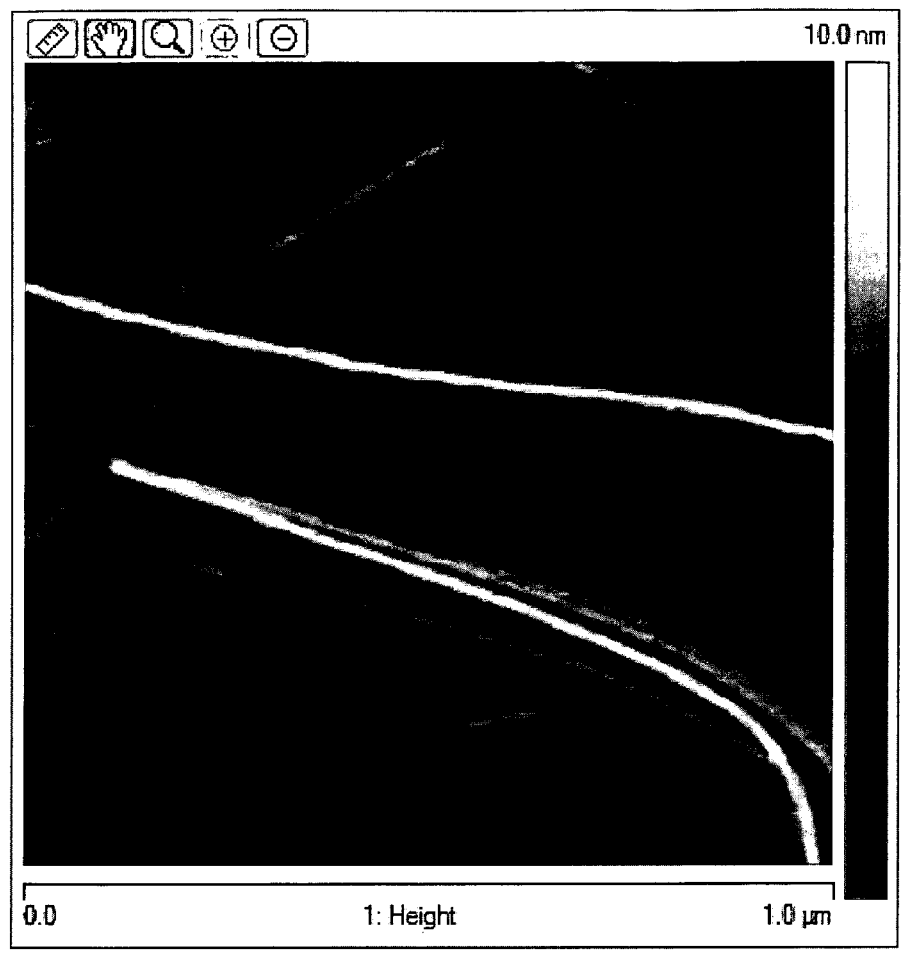
Figure 3:
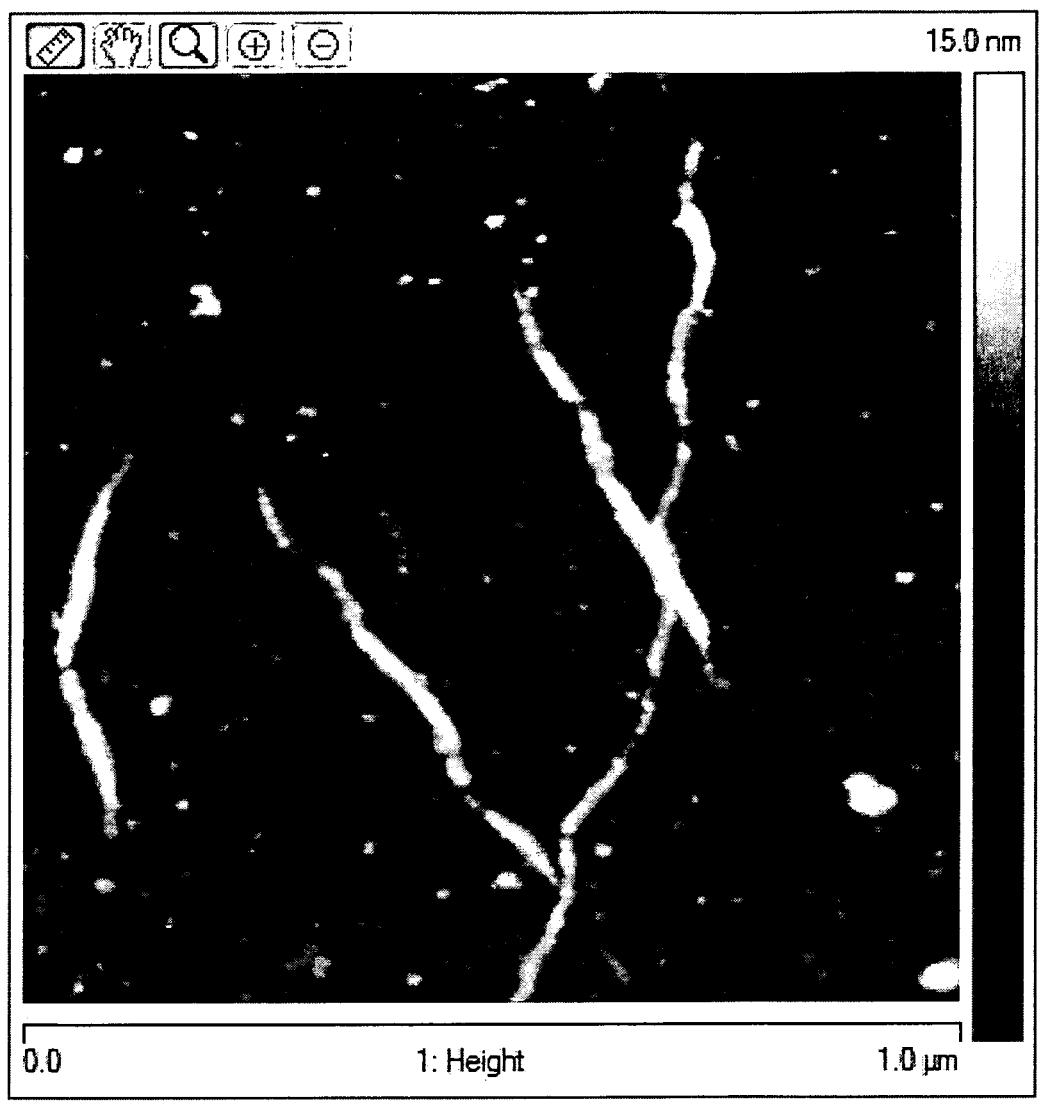
Figure 3:
Figure 3:
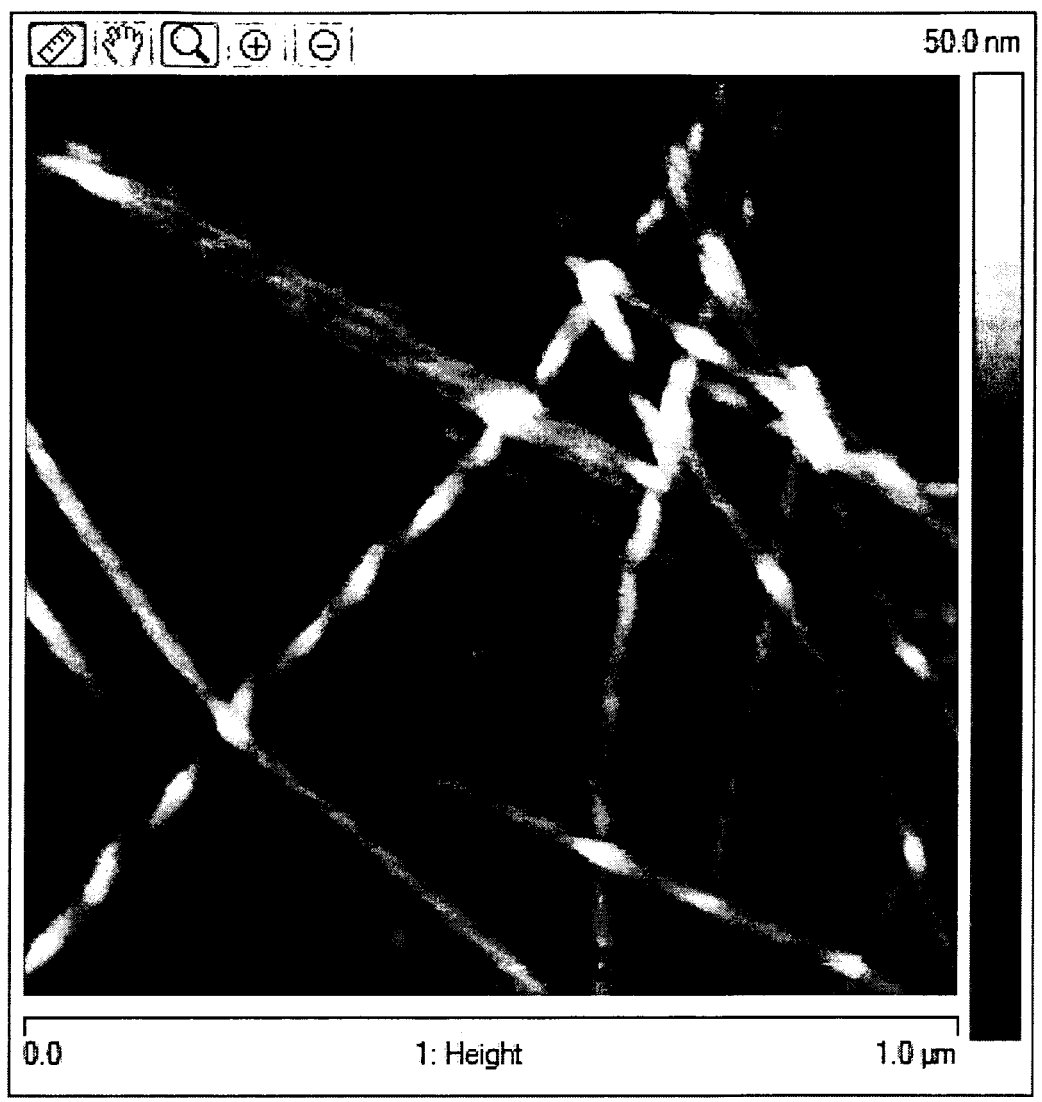
Figure 3:
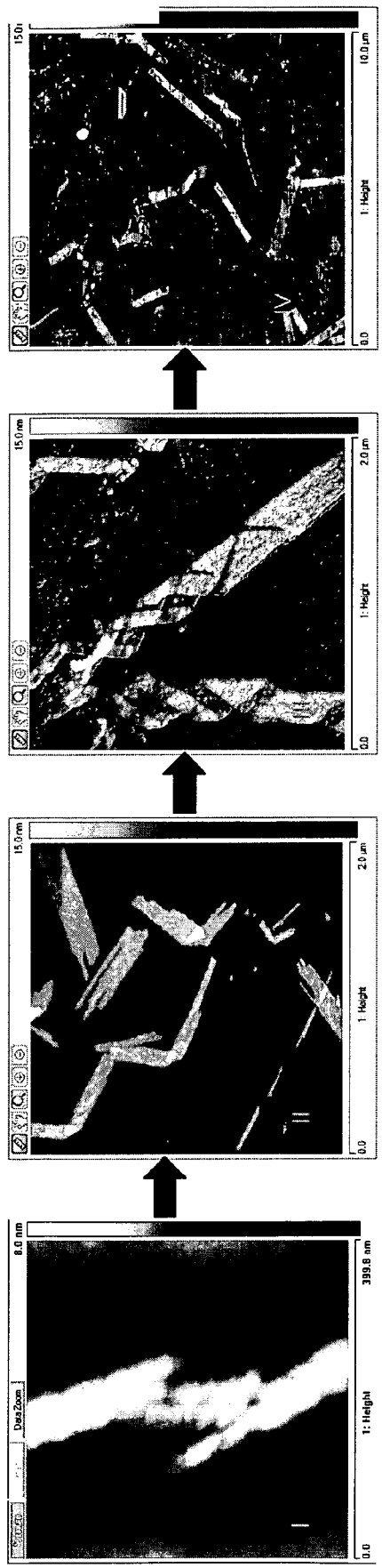

FIG. 3 shows results of Atomic Force Microscopy imaging of the tested peptides.

FIG. 3a) Self-assembling peptides B64, B65, B66 and B67 formed twisted nanofiber formations (60 nm pitch, left-handed) since 1 day post dissolution, and also self-assembled giving a hydrogel upon exposure to PBS.

FIG. 3b) Self-assembling peptides B15, B24, B32, B33, B40, B41, B42, B44, B54, B58, 59 and 61 self-assembled into flat tabular fibers;

FIG. 3c) Self-assembling peptide 4, 37 and 60 yielded twisted fibers;

FIG. 3d) Self-assembling peptides B10, B11, B12, B13 and B43 are shown and form twisted fibers;

FIG. 3e) Self-assembling peptides B18, B19, B25, B28, B29, 30, 31, B45, B52, B51, B53 and B50 are shown and form twisted fibers;

FIG. 3f) (i) B3, B17, B22, B27, B34, B39, B46, B47, B48 and B57 hierarchically self-assembled into twisted protofibrils;

FIG. 3f) (ii), packed together to give ribbons;

FIG. 3f) (iii), assembled into straight tubular structures;

FIG. 3f) (iv) and re-arranged into eventual flat sheets.

Figure 4:
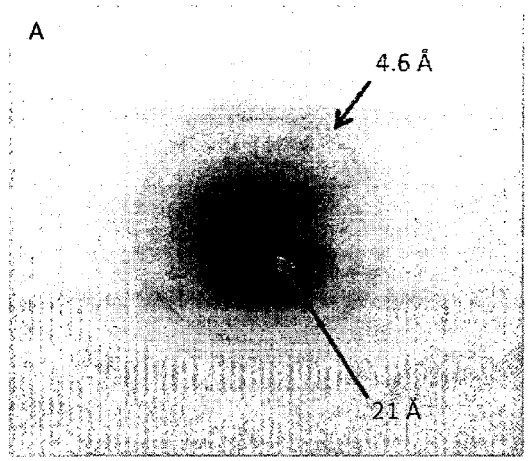
Figure 4:
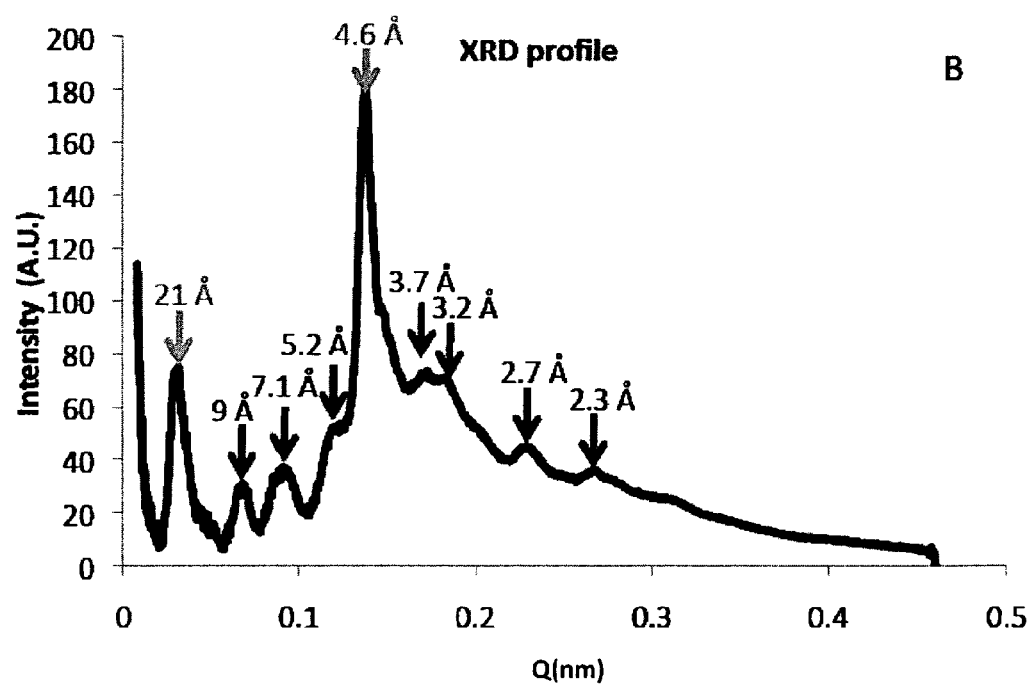
Figure 4:
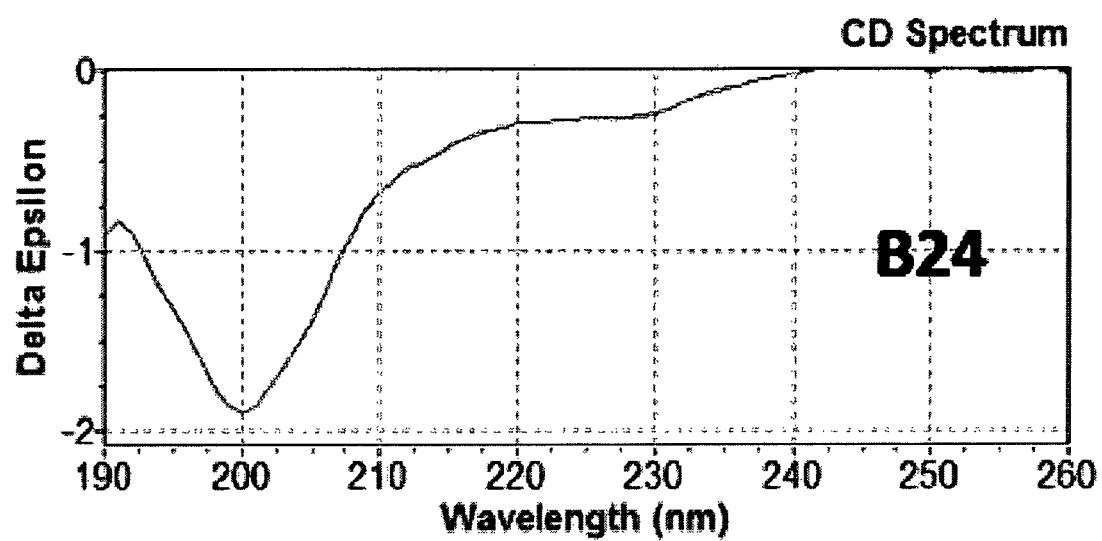

FIG. 4 (a) shows X-ray diffraction pattern.

FIG. 4 (b) radial integrated diffracted intensity recorded for B3 peptide. Most significant peaks are identified at 21 Å and 4.6 Å, presumably indicating self-assembled fibers thickness and a predominant secondary β-sheet structure respectively. Peak at 5.2 Å can be ascribed at distance between stacked aromatic groups. 3.7 Å peak can be interpreted as chains packing at VDW distance.

FIG. 4 (c) intensity peaks are summarized for twelve peptides. The strongest peak is at 4.6 Å while peaks at 3.7 Å and 2.35 Å are shared by all tested peptides.

FIG. 4 (d) the CD spectra of peptide B24 showed approximately 35% of random coil and 60% of beta-structures (210-230 nm wavelength region).

Similar results were obtained for the other tested peptides.

Figure 5:
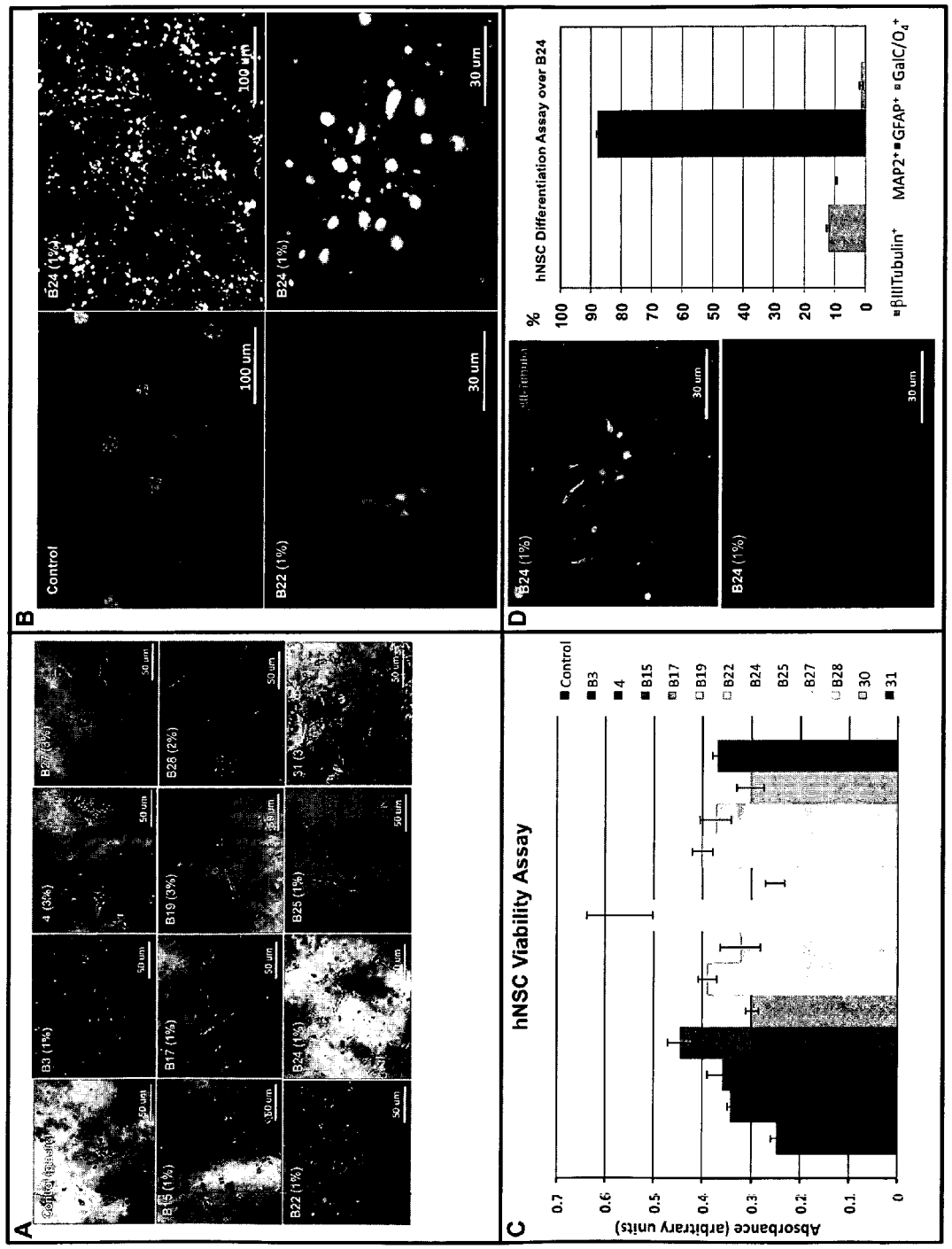

FIG. 5 shows the results of cell culture experiments are shown. hNSCs were cultured for 7 days in vitro on self-assembled scaffolds from solutions and various peptide concentrations of B3, 4, B15, B17, B19, B22, B24, B25, B27, B28 and 31.

FIG. 5 (a) Imaged cell morphologies comprise branched and adhered cells, in case of B24, or single spherical cells, as depicted in 30 and in the negative control (plastic).

FIG. 5 (b) Live/dead cell assays showed spherical clusters of living cells in the negative control as well as bipolar cells in B22 and a layer of widely branched cells in B24.

FIG. 5 (c) Cell titer assay (n=6) of cells cultured for 7 days over the above mentioned self-assembled scaffolds. Notably, B15 and B24 showed the biggest living cell populations, significantly different from negative control ($P<0.002$ and $P<0.001$ respectively; paired t-test).

FIG. 5 (d) NSCs cultured for 14 DIV over B24 scaffolds show positivity for GFAP (87.72%±0.49%), βIIITubulin (12.27%±0.49%), MAP2 (9.5%±0.1%) and GalC/O4 (1.63%±0.37%) markers (n=4).

Figure 6:
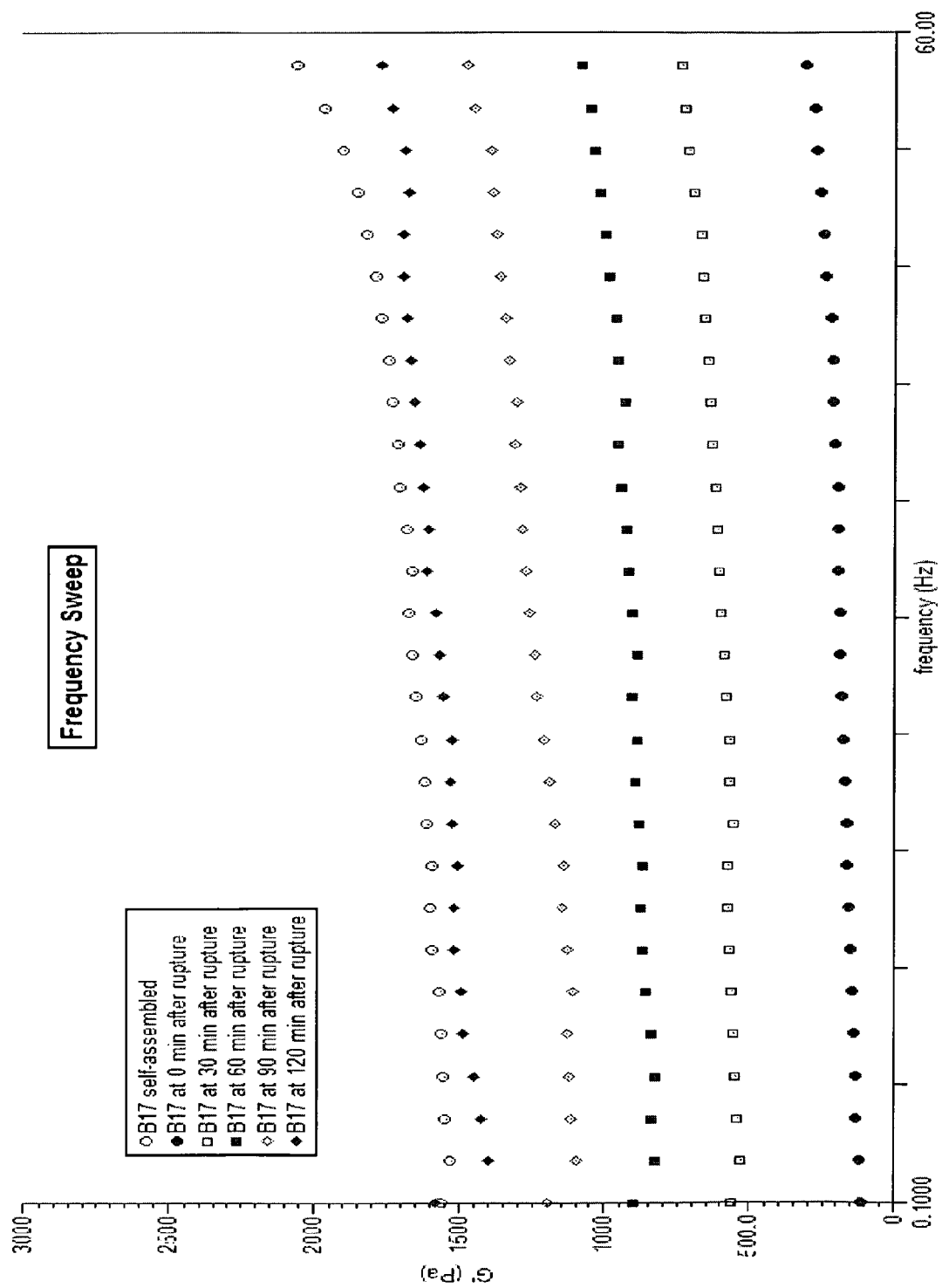
Figure 6:
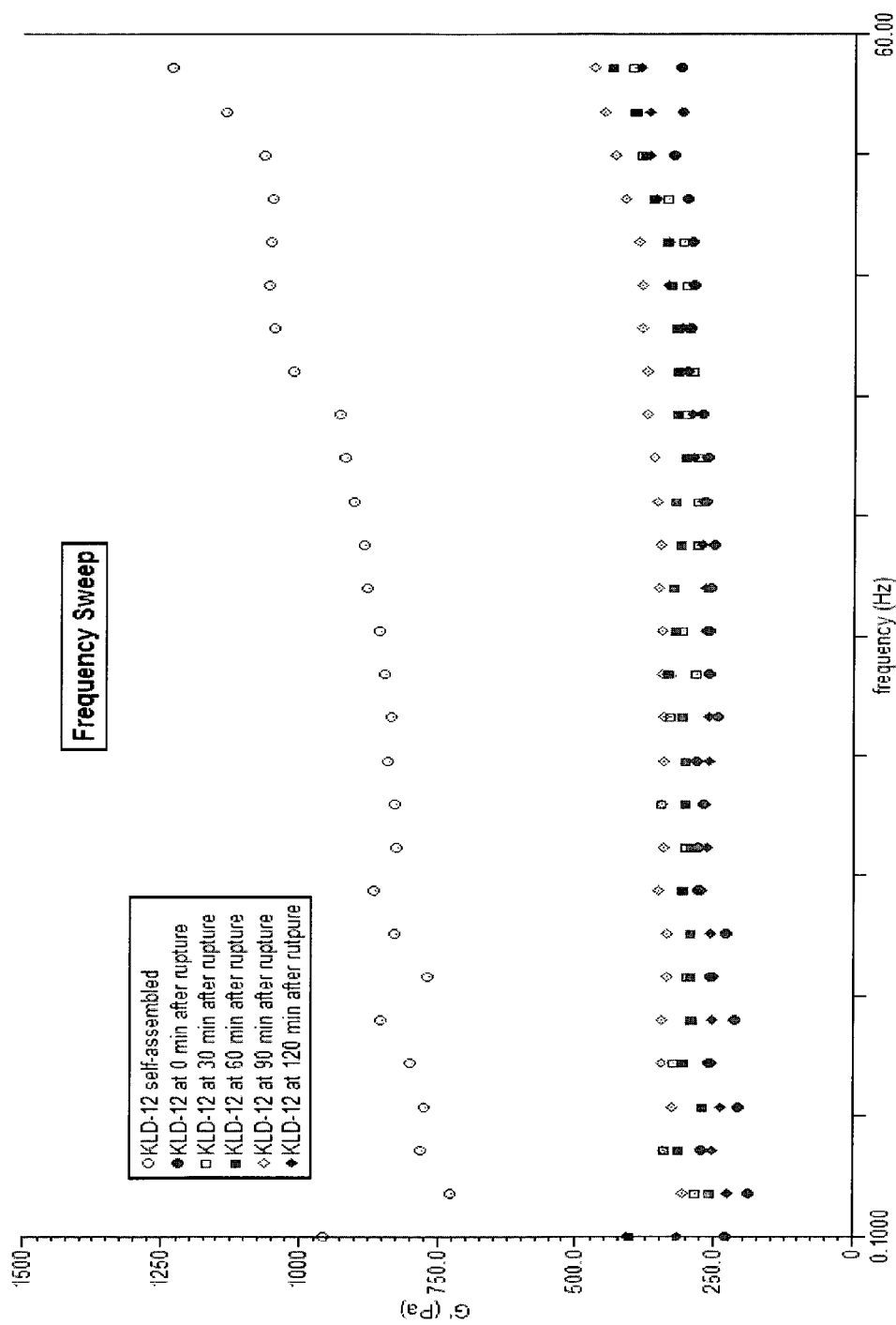

FIG. 6: Self-healing tests
FIG. 6 (a) self-healing tests for peptide B17
FIG. 6 (b) self-healing tests for peptide B25
FIG. 6 (c) self-healing tests for peptide KLD-12.

Frequency sweeps of assembled scaffold after PBS addition, after rupture and at 30 minutes subsequent time points. In (a) the storage modulus gets back to values similar to those of the assembled scaffold before rupture in 120 minutes, in (c) G' values after rupture are stable. Time sweep test of assembled scaffold of B25 after addition of PBS (b): G' values after rupture recovered in 100 minutes and steadily plateaued after recovery.

Figure 7:
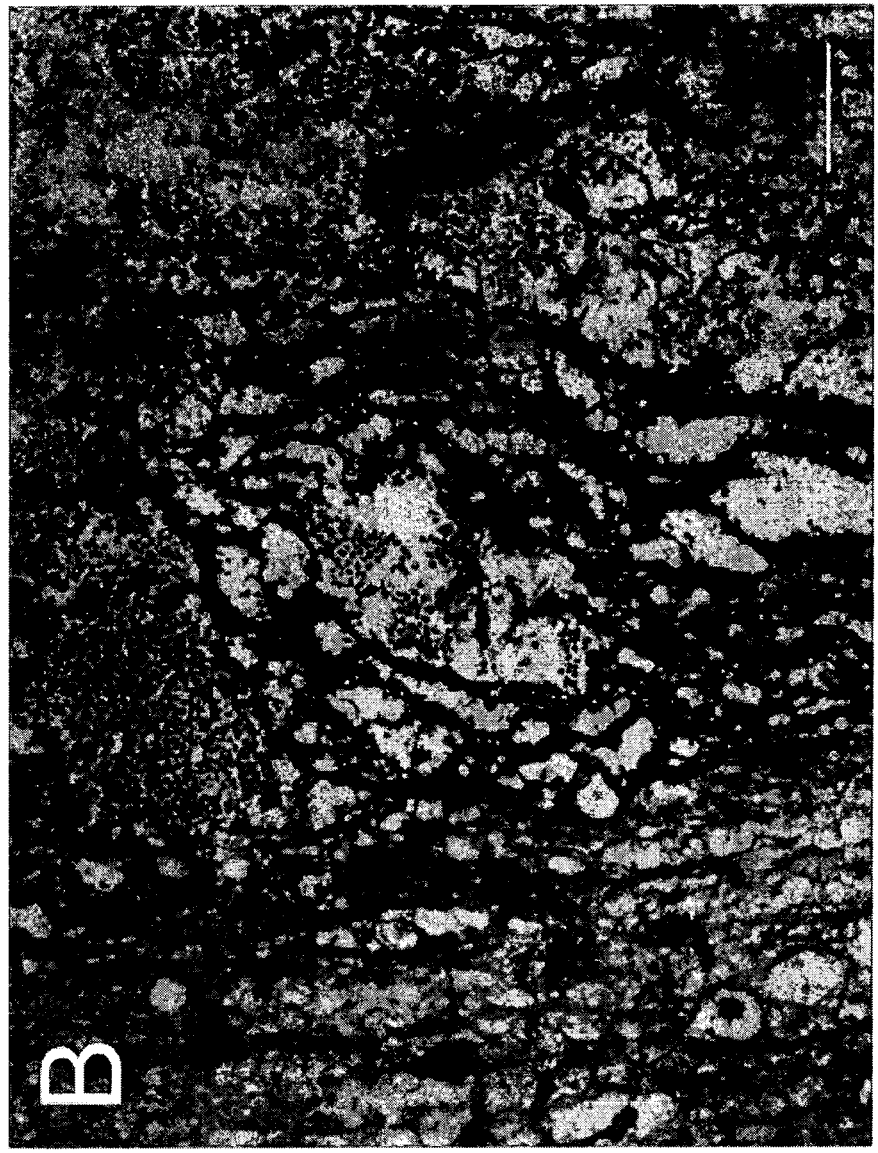
Figure 7:
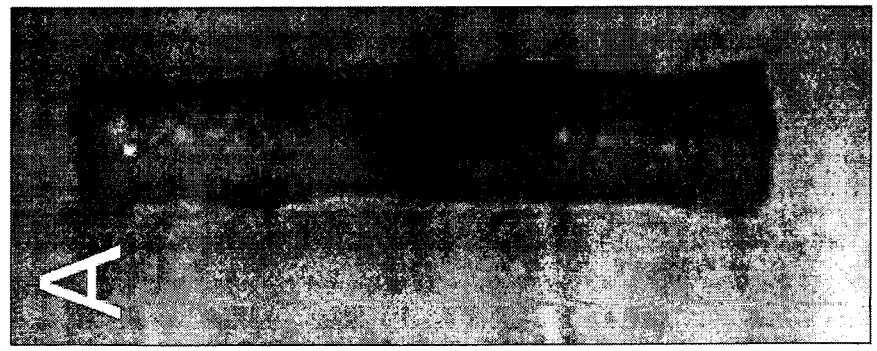
Figure 7:
Figure 7:
Figure 7:
Figure 7:
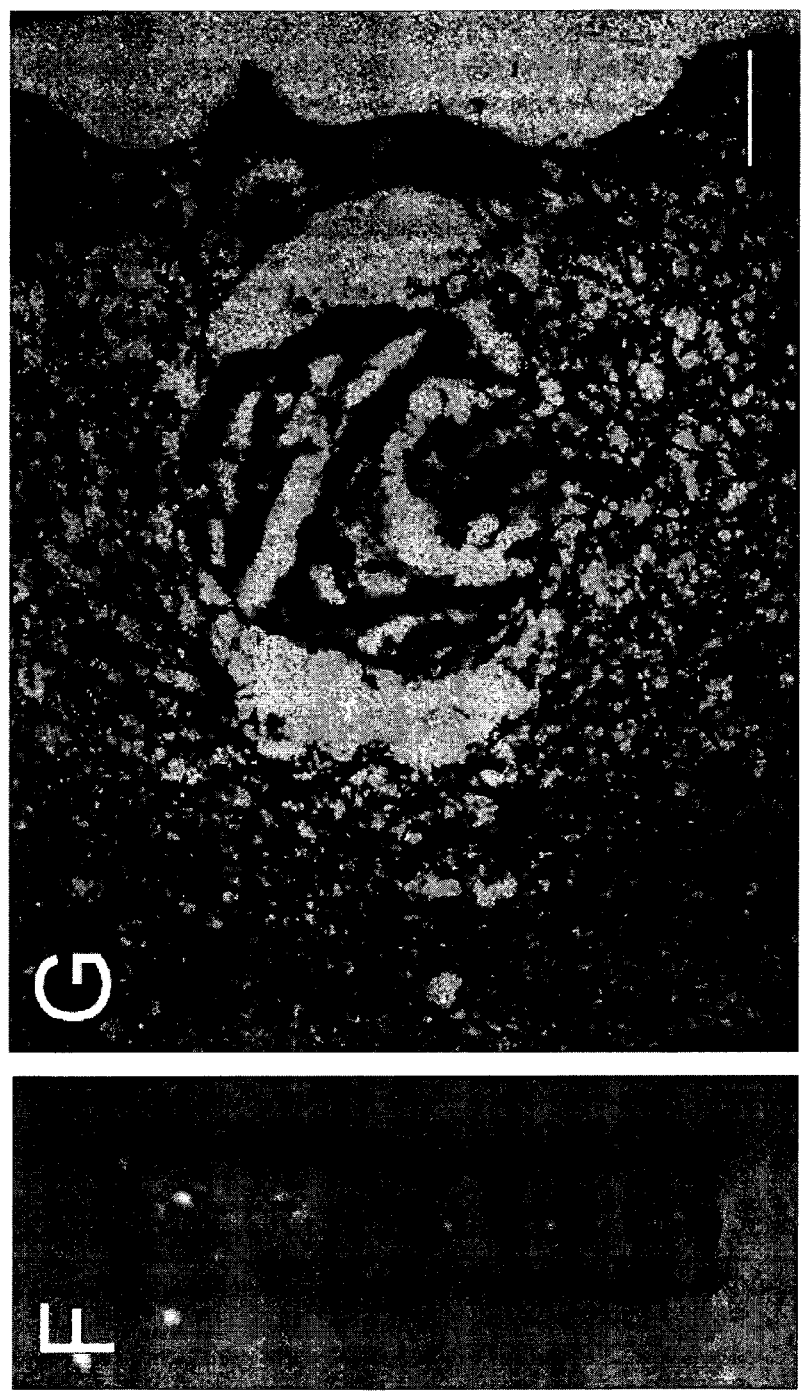
Figure 7:
Figure 7:
Figure 7:
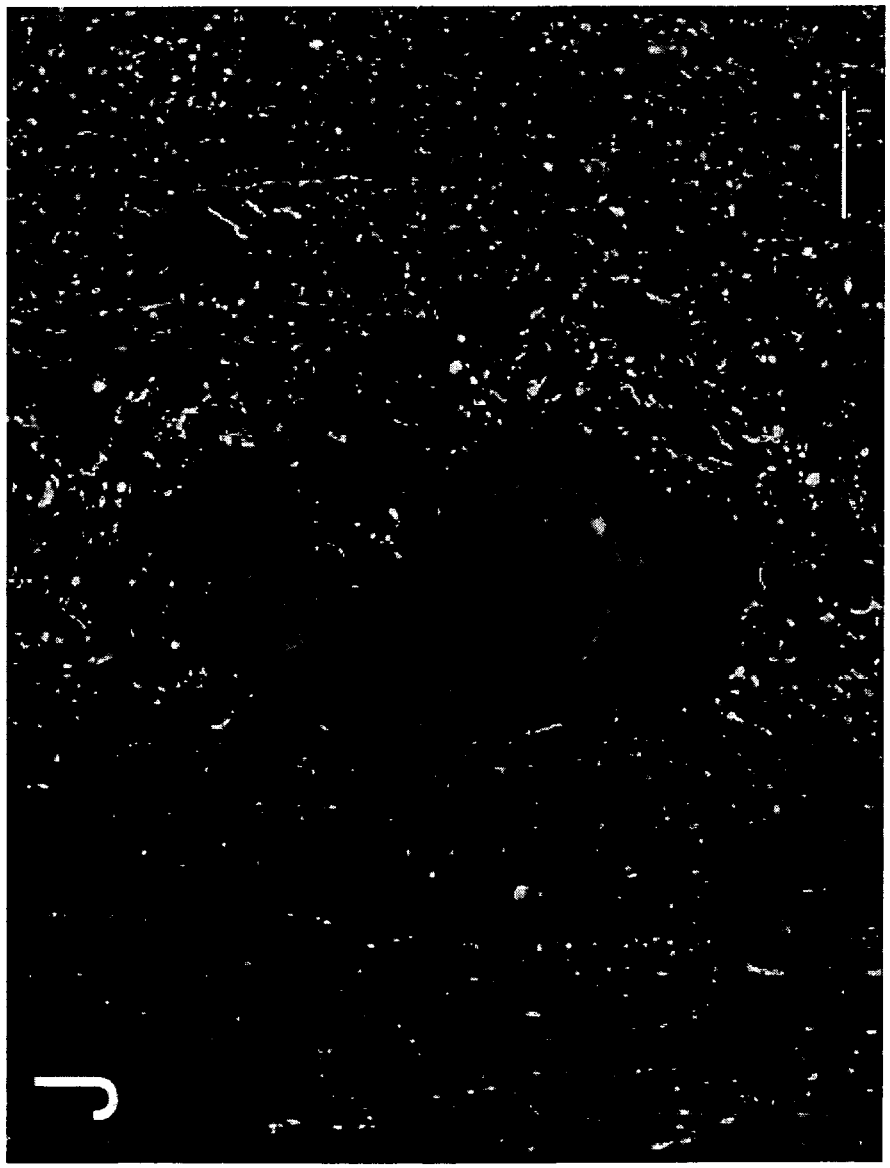

FIG. 7: B24 biocompatibility in vivo. First row: animal belonging to control group. Second row: treated animal. The hematoma spontaneously occurring in the spinal cord of saline-injected animals (A) was prevented in animal receiving injections of B24 (F). Hematoxilin-Eosin staining of the injection-site in saline-treated and in B24-treated animals (B and G respectively). In control group and in treated animals we detected similar concentrations of infiltrated macrophages (green cells in C and H respectively), apoptotic cells (green cells in D and I respectively) and degenerating nervous fibers (green cells in E and J respectively). Cell nuclei (blue) are stained with DAPI. Scale bar 100 µm.

Figure 8:
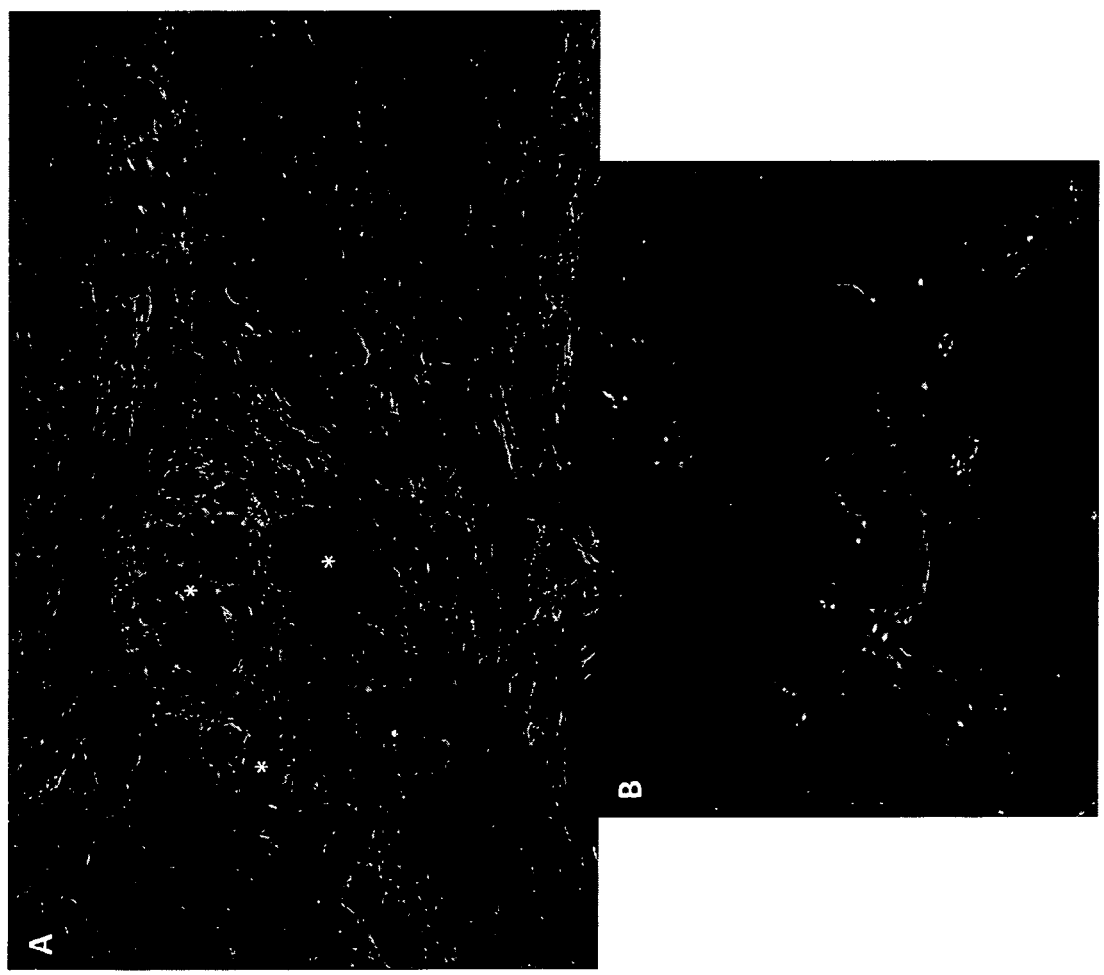

FIG. 8: B24 assessment of nervous regeneration in vivo: longitudinal sections of the spinal cords. a) nervous fibers stained for βIIITubulin and GAP-43 neuronal markers infiltrated the injected self-assembled scaffold of B24 at 1 months after is surgery (asterisks point at the scaffold). b) high-magnified image depicting bundles of regenerating nervous fibers within the implanted scaffold. Cell nuclei are marked with DAPI.

DETAILED DESCRIPTION OF THE INVENTION

The self-assembling peptide (SAP) of the present invention consists of an amino acid domain, having from 7 to 17 aminoacids, said domain being:

-GGGPFSSTKT- SEQ ID N. 1
-WGGGPFSSTKT- SEQ ID N. 2
-GGGPFSSTDT- SEQ ID N. 3
-GGGPFSSTNT- SEQ ID N. 4
-GGGPFSSTET- SEQ ID N. 5
-GGGPFSSTQT- SEQ ID N. 6
-GGGAFSSTKT- SEQ ID N. 7
-GGGPFSETKT- SEQ ID N. 8
-GGGAFSSTKTGRGD- SEQ ID N. 9
-GGGPFSSTRT- SEQ ID N. 10
-GGGAFASTKT- SEQ ID N. 11
-GGGGGPFSSTKT- SEQ ID N. 12
-GGGPWSSTKT- SEQ ID N. 13
-GGG(Propylamine)FSSTKT- SEQ ID N. 14
-WGGGAFASTKT- SEQ ID N. 15
-WGGGAFSSTKT- SEQ ID N. 16
-GGGKFSSTPT- SEQ ID N. 17
-GGGPKSSTFT- SEQ ID N. 18
-GGGPFSSKTT- SEQ ID N. 19
-GGGPFSSTTK- SEQ ID N. 20
-GGGGPFSSTKT- SEQ ID N. 21
-GGGPFSSTKTGRGD- SEQ ID N. 22
-GPFSSTKT- SEQ ID N. 23
-GGGAWASTKT- SEQ ID N. 24
-GGGAFASTKA- SEQ ID N. 25
-GGGPFSSTKTP- SEQ ID N. 26
-FGGGPFSSTKT- SEQ ID N. 27
-GGGPYSSTKT- SEQ ID N. 28
-GGGAASSTKT- SEQ ID N. 29
-GGGAFAATKT- SEQ ID N. 30
-GGGAFASAKA- SEQ ID N. 31
-GGGPFSSTAT- SEQ ID N. 32
-GGGAFAAAKA- SEQ ID N. 33
-GGGPFSSAKT- SEQ ID N. 34
-GGGPFSATKT- SEQ ID N. 35
-GGGPFSCTKT- SEQ ID N. 36
-GGGPFCSTKT- SEQ ID N. 37
-GAFASTKT- SEQ ID N. 38
-GGGGGAFASTKT- SEQ ID N. 39
-GGGAFASTKTGRGD- SEQ ID N. 40
-GGGPFSSTKTGIKVAV- SEQ ID N. 41
-GGGAFASTKTGIKVAV- SEQ ID N. 42
-GGGAFAK- SEQ ID N. 43
-(GGG)$_2$-KFSSTKT- SEQ ID N. 44
-FGGGAFASTKTGIKVAV- SEQ ID N. 45
-YGGGPFSSTKT-; SEQ ID N. 46
or
-FGGGAFSSTKT-. SEQ ID N. 47

As above mentioned, for the purposes of the present invention, each peptide has a peptide number and a corresponding SEQ ID NO., according to the following Table 1:

TABLE 1

| Peptide number | SEQ ID NO. | SAP amino acid sequence | derivated SAP amino acid sequence |
|---|---|---|---|
| B32 | SEQ ID NO. 1 | GGGPFSSTKT | Biot-GGGPFSSTKT-CONH2, Ac-GGGPFSSTKT-CONH2 |
| 4 | SEQ ID NO. 2 | WGGGPFSSTKT | Ac-WGGGPFSSTKT-CONH2 |
| B10 | SEQ ID NO. 3 | GGGPFSSTDT | Biot-GGGPFSSTDT-CONH2 |
| B11 | SEQ ID NO. 4 | GGGPFSSTNT | Biot-GGGPFSSTNT-CONH2 |
| B12 | SEQ ID NO. 5 | GGGPFSSTET | Biot-GGGPFSSTET-CONH2 |
| B13 | SEQ ID NO. 6 | GGGPFSSTQT | Biot-GGGPFSSTQT-CONH2 |
| B15 | SEQ ID NO. 7 | GGGAFSSTKT | Biot-GGGAFSSTKT-CONH2 |
| B17 | SEQ ID NO. 8 | GGGPFSETKT | Biot-GGGPFSETKT-CONH2 |
| B19 | SEQ ID NO. 9 | GGGAFSSTKTGRGD | Biot-GGGAFSSTKTGRGD-CONH2 |
| B22 | SEQ ID NO. 10 | GGGPFSSTRT | Biot-GGGPFSSTRT-CONH2 |
| B24 B55 | SEQ ID NO. 11 | GGGAFASTKT | Biot-GGGAFASTKT-CONH2 Biot-GGGAFASTKT-COOH |
| B25 | SEQ ID NO. 12 | GGGGGPFSSTKT | Biot-GGGGGPFSSTKT-CONH2 |
| B27 | SEQ ID NO. 13 | GGGPWSSTKT | Biot-GGGPWSSTKT-CONH2 |
| B28 | SEQ ID NO. 14 | GGG(Propylamine)FSSTKT | Biot-GGG(Propylamine)FSSTKT-CONH2 |
| 30 | SEQ ID NO. 15 | WGGGAFASTKT | Ac-WGGGAFASTKT-CONH2 |
| 31 | SEQ ID NO. 16 | WGGGAFSSTKT | Ac-WGGGAFSSTKT-CONH2 |
| B64 | SEQ ID NO. 17 | GGGKFSSTPT | Biot-GGGKFSSTPT-CONH2 |
| B65 | SEQ ID NO. 18 | GGGPKSSTFT | Biot-GGGPKSSTFT-CONH2 |
| B66 | SEQ ID NO. 19 | GGGPFSSKTT | Biot-GGGPFSSKTT-CONH2 |
| B67 | SEQ ID NO. 20 | GGGPFSSTTK | Biot-GGGPFSSTTK-CONH2 |
| B38 | SEQ ID NO. 21 | GGGGPFSSTKT | Biot-GGGGPFSSTKT-CONH2 |
| B18 | SEQ ID NO. 22 | GGGPFSSTKTGRGD | Biotin-GGGPFSSTKTGRGD-CONH2 |
| B29 | SEQ ID NO. 23 | GPFSSTKT | Biotin-GPFSSTKT-NH2 |
| B32 | SEQ ID NO. 24 | GGGAWASTKT | Biotin-GGGAWASTKT-NH2 |
| B33 | SEQ ID NO. 25 | GGGAFASTKA | Biotin-GGGAFASTKA-NH2 |
| B34 | SEQ ID NO. 26 | GGGPFSSTKTP | Biotin-GGGPFSSTKTP-NH2 |
| 37 | SEQ ID NO. 27 | FGGGPFSSTKT | Ac-FGGG-PFSSTKT-CONH2 |
| B39 | SEQ ID NO. 28 | GGGPYSSTKT | Biotin-GGG-PYSSTKT-CONH2 |
| B40 | SEQ ID NO. 29 | GGGAASSTKT | Biotin-GGG-AASSTKT-CONH2 |
| B41 | SEQ ID NO. 30 | GGGAFAATKT | Biotin-GGG-AFAATKT--CONH2 |
| B42 | SEQ ID NO. 31 | GGGAFASAKA | Biotin-GGG-AFASAKA-CONH2 |
| B43 | SEQ ID NO. 32 | GGGPFSSTAT | Biotin-GGG-PFSSTAT-CONH2 |
| B44 | SEQ ID NO. 33 | GGGAFAAAKA | Biotin-GGG-AFAAAKA-CONH2 |
| B45 | SEQ ID NO. 34 | GGGPFSSAKT | Biotin-GGG-PFSSAKT-CONH2 |
| B46 | SEQ ID NO. 35 | GGGPFSATKT | Biotin-GGG-PFSATKT-CONH2 |
| B47 | SEQ ID NO. 36 | GGGPFSCTKT | Biotin-GGG-PFSCTKT-CONH2 |
| B48 | SEQ ID NO. 37 | GGGPFCSTKT | Biotin-GGG-PFCSTKT-CONH2 |

TABLE 1-continued

| Peptide number | SEQ ID NO. | SAP amino acid sequence | derivated SAP amino acid sequence |
|---|---|---|---|
| B50 | SEQ ID NO. 38 | GAFASTKT | Biotin-G-AFASTKT-CONH2 |
| B51 | SEQ ID NO. 39 | GGGGGAFASTKT | Biotin-GGGGG-AFASTKT-CONH2 |
| B52 | SEQ ID NO. 40 | GGGAFASTKTGRGD | Biotin-GGG-AFASTKT-GRGD-CONH2 |
| B53 | SEQ ID NO. 41 | GGGPFSSTKTGIKVAV | Biotin-GGG-PFSSTKT-GIKVAV-CONH2 |
| B54 | SEQ ID NO. 42 | GGGAFASTKTGIKVAV | Biotin-GGG-AFASTKT-GIKVAV-CONH2 |
| B57 | SEQ ID NO. 43 | GGGAFAK | Biotin-GGG-AFAK-CONH2 |
| B58 | SEQ ID NO. 44 | (GGG)2-KFSSTKT | (Biotin-GGG)2-K-FSSTKT-CONH2 |
| 59 | SEQ ID NO. 45 | FGGGAFASTKTGIKVAV | Ac-F-GGG-AFASTKT-GIKVAV-CONH2 |
| 60 | SEQ ID NO. 46 | YGGGPFSSTKT | Ac-Y-GGG-PFSSTKT-CONH2 |
| 61 | SEQ ID NO. 47 | FGGGAFSSTKTGGGPFSSTKT | Ac-F-GGG-AFSSTKT-CONH2 |

The self-assembling peptides (SAPs) of the present invention have the amino acid sequences defined in Table 1, in which the one letter IUPAC amino acid code is used (i.e. G corresponds to the amino acid Glycine, P corresponds to the amino acid Proline). Each SAP has a peptide number and a corresponding SEQ ID NO., as above reported in the Table 1.

Each SAP has a corresponding derivated SAP, which is the amino acid sequence with the Biotinilation or Acetilation at the N-terminus and C-terminal amides.

The biotinylated peptides are named with 'B+number'. The other peptides are just numbered.

The SAPs of the present invention are optionally biotinylated and unbiotinylated sequences at the N-termini and amidated or not at the C-termini, hybrid peptide-peptoid sequences, for a total of 47 tested motifs. The SAPs of the present invention are all linear peptides, with the exception of SEQ ID NO.44 which is a branched peptide with two identical GGG branches.

The subject of the invention is therefore a novel group of low molecular weight self-assembling peptides.

These self-assembling peptides are of synthetic origin and are therefore easy to manufacture in large quantities, and they can be modified chemically and biologically. Such modifications give scientists the chance to construct an ultrastructure promoting cell adhesion and growth.

These peptides have the advantages of being of synthetic origin, and therefore do not have the disadvantages seen in natural peptides such as the tendency to induce inflammatory response and pathogen transfer due to undefined factors that cannot be eliminated by purification prior to implantation, the significant degree of variability between different lots and the difficulty of availability of large scale sources.

The low molecular weight self-assembling peptides of the invention can form hydrogels which are synthetic but naturally inspired and surprisingly form nanostructured materials of easy functionalization and capable of creating microenivorments suited for culturing cells, triggering tissue regeneration and other applications beyond life-sciences such as electrochemical sensing, self-assembling circuits and transistors for computers and construction of three-dimensional nanoscale systems.

Upon exposure to a neutral pH buffer the initial spontaneous, and concentration dependant, self-assembling process is speeded up toward the formation of solid scaffolds, whose stiffness, depending on the peptide sequence, span three orders of magnitude.

Surprisingly the SAPs according to the present invention spontaneously form a number of different and hierarchical aggregated nano- and micro-structures, even though they present such a group of heterogeneous sequences. These peptides assemble into beta-structures (beta-sheets and beta-turns), present aromatic interactions between Phe residues and the tails of the fibers, electrostatic repulsions (Lys allows to obtain a pH-driven self-assembly), h-bonds formations (Ser,Thr). In most of the peptides pH speed up the self-assembly phenomena spontaneously occurring in water.

The peptides of the present invention surprisingly show a self-healing propensity at the mesoscale, indeed hydrogels re-form solid scaffolds, recovering their initial stiffness, after mechanical rupture.

In fact, in terms of recovery of stiffness of the self-assembled scaffolds, the peptides of the invention self-assemble at multiple hierarchical levels.

The peptides for which self-healing property has been seen are for example B3, 4, B15, B17, B22, B24, B25, B27 and 31 (SEQ ID NO. 1, 2, 7, 8, 10, 11, 12, 13 and 16) giving microscaled tubular structures that could be used for drug delivery by an useful strategy consisting in dissolving peptides in drug loaded solutions prior self-assembly, separating the assembled scaffolds via centrifugation and injecting the self-healing assembled scaffolds in vivo.

In a preferred embodiment the self-assembling peptide has an amino acid domain selected from the group consisting of SEQ ID NO. 1, 3, 4, 5, 6, 7, 8, 9, 10, 11, 12, 13, 14, 17, 18, 19, 20 and 21.

In a further preferred embodiment the self-assembling peptide of the invention has the amino acid domain consisting of SEQ ID NO. 14, wherein a propylamine is present between the G in position 3 and the F in position 4. Propylamine, also known as n-propylamine, is an amine with the chemical formula $C_3H_9N$.

In an even more preferred embodiment the self-assembling peptide has an amino acid domain selected from the group consisting of SEQ ID NO. 1, 3, 4, 5, 6, 7, 8, 9, 10, 11, 12, 13, 14, 17, 18, 19, 20 and 21 wherein the N-terminus is optionally biotinylated.

In an even more preferred embodiment the self-assembling peptide has an amino acid domain selected from the group consisting of SEQ ID NO. 1, 8, 10 and 13 wherein the N-terminus is optionally biotinylated.

In a still more preferred embodiment the self-assembling peptide has the amino acid domain of SEQ ID NO. 11, more preferably wherein the N-terminus is optionally biotinylated.

In a further embodiment the self-assembling peptide of the invention has an amino acid domain selected from the group consisting of SEQ ID NO. 2, 15 and 16.

In a still further embodiment the self-assembling peptide of the invention has an amino acid domain selected from the group consisting of SEQ ID NO. 2, 15 and 16 wherein the N-terminus is acetylated.

In a still further embodiment the self-assembling peptide of the invention has an amino acid domain selected from the group consisting of SEQ ID NO. 1, 8, 10, 12 and 13.

In a further embodiment the self-assembling peptide of the invention has a number of Glycines of the aminoacid domain of 3 to 8.

In a preferred embodiment the self-assembling peptide of the invention has a number of Glycines of the aminoacid domain of 3 to 6.

By increasing the number of Glycines of the spacers, Biotin acquires more degree of freedom allowing a better exposure and self-orientation for h-bond formation and/or stacking, thus favoring self-assembling. This is why Glycines, ranging in is number from 3 to 8, preferably from 3 to 6, can strongly influence the hierarchical formation of multiple nano- and microstructures.

In a preferred aspect, the present invention concerns the self-assembling peptide (SAP) which consists of an amino acid domain, having from 9 to 14 aminoacids, said domain being:

| | |
|---|---|
| -GGGPFSSTKT- | SEQ ID N. 1 |
| -WGGGPFSSTKT- | SEQ ID N. 2 |
| -GGGPFSSTDT- | SEQ ID N. 3 |
| -GGGPFSSTNT- | SEQ ID N. 4 |
| -GGGPFSSTET- | SEQ ID N. 5 |
| -GGGPFSSTQT- | SEQ ID N. 6 |
| -GGGAFSSTKT- | SEQ ID N. 7 |
| -GGGPFSETKT- | SEQ ID N. 8 |
| -GGGAFSSTKTGRGD- | SEQ ID N. 9 |
| -GGGPFSSTRT- | SEQ ID N. 10 |
| -GGGAFASTKT- | SEQ ID N. 11 |
| -GGGGGPFSSTKT- | SEQ ID N. 12 |
| -GGGPWSSTKT- | SEQ ID N. 13 |
| -GGG(Propylamine)FSSTKT- | SEQ ID N. 14 |
| -WGGGAFASTKT- | SEQ ID N. 15 |
| -WGGGAFSSTKT- | SEQ ID N. 16 |
| -GGGKFSSTPT- | SEQ ID N. 17 |
| -GGGPKSSTFT- | SEQ ID N. 18 |
| -GGGPFSSKTT- | SEQ ID N. 19 |
| -GGGPFSSTTK- | SEQ ID N. 20 |
| -GGGGPFSSTKT- | SEQ ID N. 21 |

In a further preferred aspect, the present invention concerns the self-assembling peptide (SAP) which consists of an amino acid domain, having from 7 to 17 aminoacids, said domain being:

| | |
|---|---|
| -GGGPFSSTKTGRGD- | SEQ ID N. 22 |
| -GPFSSTKT- | SEQ ID N. 23 |
| -GGGAWASTKT- | SEQ ID N. 24 |
| -GGGAFASTKA- | SEQ ID N. 25 |
| -FGGGPFSSTKT- | SEQ ID N. 27 |
| -GGGPYSSTKT- | SEQ ID N. 28 |
| -GGGAASSTKT- | SEQ ID N. 29 |
| -GGGAFAATKT- | SEQ ID N. 30 |
| -GGGAFASAKA- | SEQ ID N. 31 |
| -GGGPFSSTAT- | SEQ ID N. 32 |
| -GGGAFAAAKA- | SEQ ID N. 33 |
| -GGGPFSSAKT- | SEQ ID N. 34 |
| -GGGPFSATKT- | SEQ ID N. 35 |
| -GGGPFSCTKT- | SEQ ID N. 36 |
| -GGGPFCSTKT- | SEQ ID N. 37 |
| -GAFASTKT- | SEQ ID N. 38 |

-continued

-GGGGGAFASTKT- SEQ ID N. 39

-GGGAFASTKTGRGD- SEQ ID N. 40

-GGGPFSSTKTGIKVAV- SEQ ID N. 41

-GGGAFASTKTGIKVAV- SEQ ID N. 42

-GGGAFAK- SEQ ID N. 43

-(GGG)$_2$-KFSSTKT- SEQ ID N. 44

-FGGGAFASTKTGIKVAV- SEQ ID N. 45

-YGGGPFSSTKT-; SEQ ID N. 46
or

-FGGGAFSSTKT-. SEQ ID N. 47

In a preferred embodiment the invention regards a hydrogel comprising the self-assembling peptides and a hydrogelating ingredient.

According to a preferred embodiment, the self-assembling peptide polymer comprises at least 2 identical self-assembling peptides of the invention.

A further aspect of the present invention is a self-assembling peptide polymer comprising at least 2 different self-assembling peptides.

A still further embodiment of the invention regards the use of the self-assembling peptide polymer as a medicament.

The invention further regards a tabular nanofiber comprising at least 2 identical self-assembling peptides.

The invention further regards a tabular nanofiber comprising at least 2 different self-assembling peptides.

According to a further embodiment the invention regards a tabular nanofiber, characterised in that it is from 5 to 10 µm in length.

According to a still further embodiment the invention regards a complex interwoven membrane made of at least 2 tabular nanofibres.

In a still more preferred embodiment the invention regards 10 µm-long tabular nanofibres which self assemble into complex interwoven membranes of from 0.5 to 4 µm in width.

The peptides of the present invention surprisingly self-aggregate and arrange at the nanoscale in structures ranging from tabular fibers to twisted coils and hierarchically assembled sheets, showing a high mechanical stiffness of the assembled scaffolds.

A further embodiment of the invention regards therefore a self-assembled nanostructure consisting of 2 or more identical peptides.

A further embodiment of the invention regards a self-assembled nanostructure consisting of 2 or more different peptides.

A further embodiment of the invention regards the self-assembled nanostructure having a hollow cavity and the use of such a self-assembled nanostructure for the release of small molecular drugs.

Such small molecular drugs can be confined in scaffold hollow cavities and eventually interact weakly with the net surface charges of the self-assembled nanostructures thus being released slowly.

Additionally, being some biotins available for binding with streptavidin (tagging tests were successfully conducted in vivo to track bioabsorption time in animals), biotinylated peptides can be functionalized, by using streptavidin or avidin as linkers, with additional biotinylated functional motifs or biotinylated drugs or cytokines to obtain a slow delivery in vivo.

In a still more preferred embodiment the invention regards a pharmaceutical composition comprising at least one polymer according to the invention and a pharmaceutically bioactive excipient.

Exemplary pharmaceutically acceptable excipients include any and all solvents, is dispersion media, diluents, or other liquid vehicles, dispersion or suspension aids, surface active agents, isotonic agents, thickening or emulsifying agents, preservatives, solid binders, lubricants and the like, as suited to the particular form of administration and dosage.

Further the invention regards the use of the hydrogel for use as a scaffold for in vitro cell culture.

Further the invention regards the use of the hydrogel for in vitro cell culture in 2 and 3 dimensions. These hydrogels are very similar to the fibrous component of the extra cellular matrix, which makes them capable of supporting cell cultures in two dimensions (2-D) and three dimensions (3-D).

A further aspect of the invention is the use of the hydrogel according to the invention as a scaffold for the in vitro growth and differentiation of human neural stem cells (hNSCs) to assess their potential for in vitro cell cultures and in vivo nervous tissue regeneration.

A still further aspect of the invention is the use of the hydrogel according to the invention as a scaffold for the in vitro growth and differentiation of murine neural stem cells (hNSCs) to assess their potential for in vitro cell cultures and in vivo nervous tissue regeneration.

In a still further aspect the invention regards the use of the hydrogel according to the invention for in vivo nervous regeneration.

In a still further aspect the invention regards the use of the hydrogel according to the invention for hemostasis.

In a still further aspect the invention regards the use of the hydrogel according to claim 4 in regenerative medicine applications and for delivering drugs in vivo, for tissue engineering and for triggering tissue regeneration.

A self-assembling peptide of the invention, may be used to treat a variety of tissue defects and diseases. Hydrogels, either with or without cells growing on the surface or encapsulated within may be implanted into the body, e.g., surgically or using any other type of suitable procedure. Other routes, including oral, percutaneous, intramuscular, intravenous, and subcutaneous may be employed. One of ordinary skill in the art will be able to select an appropriate delivery technique.

In general, SAPs of the invention may be useful in any situation involving injury or damage to tissue. Such injury may occur as a result of surgery, trauma, tumor, degenerative disease, or other diseases or conditions. The injury may, but need not, involve death of cells. The SAPs are useful to restore structural and/or functional integrity to the tissue, i.e., to aid in restoring the tissue to the functional or structural condition that existed prior to the injury. Certain injuries may result in physical barriers that can impede regeneration or repair of tissue. Such barriers may include areas of necrosis, cavitation, or scar tissue formation. In certain embodiments of the invention introducing the materials described herein at a site of injury allows cell or tissue growth from a location proximal to the site of injury or barrier to a location distal to the site of injury or barrier.

Certain SAPs of the present invention may be used to ameliorate the effects of disease or degeneration of an organ, to repair an injury to an organ or other body structure or to form an organ or other body structure. Such organs or body structures include, but are not necessarily limited to, vascular tissue, brain, nervous tissue, peripheral nerves, cartilage, esophagus, fallopian tube, heart, intestines, gallbladder, kidney, liver, lung, ovaries, pancreas, prostate, bladder, bone, spinal cord, spleen, stomach, testes, thymus, thyroid, trachea, ureter, urethra, uterus, and skin.

The present SAPs may also be used in dermatology as fillers for use in aesthetical and cosmetic techniques, to counteract wrinkles and the most common signs of ageing.

SAPs according to the present invention can be used in particular in the form of hydrogels, as filling materials in order to restore the skins youthful aspect, and reduce fine lines and wrinkles.

In general, a variety of devices may be used to introduce the hydrogels of the invention at the site of injury. Delivery via a syringe is one convenient technique. SAPs can also be introduced by catheter or directly at a site of surgery. In other embodiments of the invention hydrogel formation is allowed to occur in vitro and the hydrogel is introduced into the body.

The self-assembling peptides of the invention may be used to promote formation of a layer of vascular endothelium at a site of injury, e.g., following a procedure such as angioplasty. They can also be used as coating materials, e.g., for devices such as vascular grafts or stents, to promote endothelialization. In an alternate approach, the SAPs form a layer on the inner surface of an artificial conduit such as an artificial blood vessel. Endothelial cells are cultured on the layer formed by the self-assembled peptides for a period of time. The cells secrete ECM components. The cells may then be removed, leaving behind an intact basement membrane layer containing ECM molecules synthesized by the cells.

A still further aspect of the invention is the use of such peptides as molecular switches or devices sensitive to pH, concentration and temperature.

The self-assembling phenomena of the novel peptides obtained are illustrated and demonstrated in the Examples 1-6 described in the present invention.

Example 1

Synthesis and Purification of Peptides of the Present Invention

Each peptides of the present invention was synthesized on a 0.05 mmol scale with standard fluorenyl methoxy carbonyl solid-phase techniques using an AAPTEC peptide synthesizer. Rink amide resin (0.6 mmol/g substitution) was used to produce C-terminal amides; amino acids were dissolved in 0.4 M NMP with 0.4 M HoBt; 0.5 M Biotin with 0.4 M HoBt in DMSO solution was used for biotinylation step.

The peptides were then cleaved from the resin and deprotected with 4 ml of 95% trifluoroacetic acid (TFA), 2.5% water and 2.5% triisopropylsilane. The cleaved peptides were precipitated, washed several times with cold diethyl ether and dissolved in 20-25% of acetonitrile solution prior to be lyophilized and stored at −20° C. Crude peptides were analyzed and purified by reverse phase HPLC using a Varian Galaxie system equipped with an analytical and semi-preparative C18 columns. Eluents were 0.1% (v/v) TFA in water (Buffer A) and 0.1% (v/v) TFA in acetonitrile (Buffer B). Starting conditions were 0% buffer A and 100% buffer B and the gradient developed with a linear increase in buffer B. In 40 minutes gradient went to 45% buffer B. Molecular weight of the peptides was confirmed with MALDI-TOF mass spectrometry (4800 Applied Biosystems).

Figure 1:
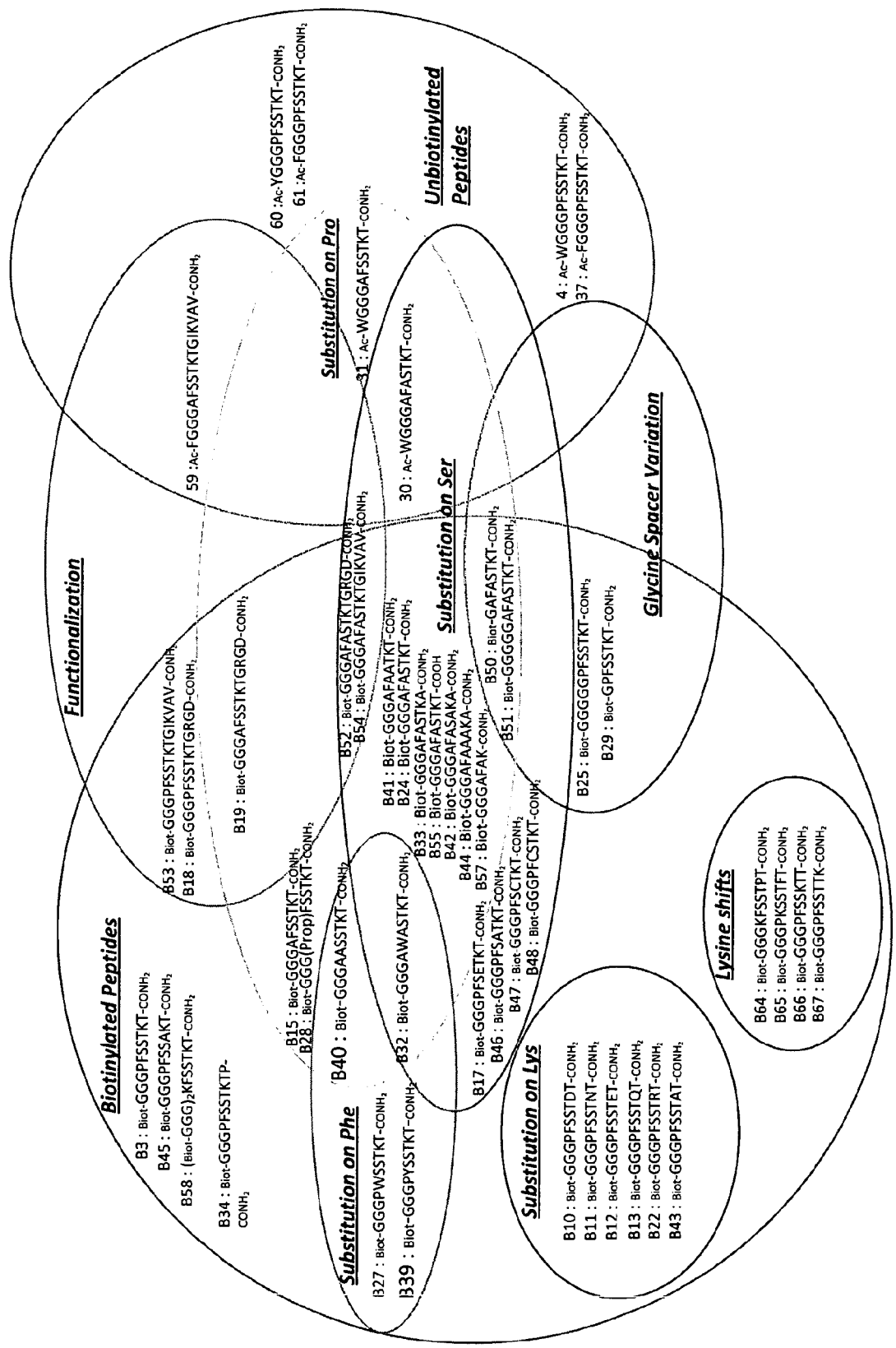
FIG. 1 shows an 'a priori' classification of the tested sequences.

Schematic Representation of the Main Sequence Variations in FIG. 1.

The acetylated BMHP sequence (Ac-PFSSTKT-CONH2) and a Gly added version (Ac-GGGPFSSTKT-CONH2) were synthesized and purified to assess their propensity in forming membranes or scaffolds when dissolved in distilled water and in phosphate-buffered saline solution (PBS) pH 7.4 at the macroscale.

Biotin, a water-soluble vitamin, acts as a cofactor in a number of important biochemical metabolic reactions and pathways related to cell signalling, gene expression, and chromatin structure (10). Multiple conformational ensembles of biotin, ranging from extended to folded states, have been found in solution (11). The latter structures are stabilized by hydrogen bonding between the ureido group and the valeryl carboxylic acid side chain. SEQ ID NO.1 was tagged with biotin (peptide B3: Biot-GGGPFSSTKT-CONH2), obtaining a viscous and opaque solution (at 3% w/v concentration) shifting to solid scaffold when exposed to neutral pH buffer. Consequently, in order to asses the importance of each residue/feature of the discovered SAP 48 additional new peptides representing specific variations of peptide B3 (FIG. 1) were synthesized.

In detail, biotin was replaced with tryptophan (peptides 4, 30, 31), with phenylalanine (peptides 37, 59, 61) or with tyrosine (peptide 60). Other modifications comprise proline substitution with alanine (peptides B15, B19, B24, and 31, B32, B33, B40, B41, B42, B44, B50, B51, B52, B54, B55, B57) or with propylamine (peptide B28) to give more linearity to the molecule backbone. B28 (SEQ ID NO. 14) has a peptoid residue, a propylamine, which is inserted between the G in position 3 and the F in position 4 instead of a proline aminoacid: this guarantees the same number of carbon atoms of side chain without the characteristic α-carbon of proline. The choice of testing propylamine was made in optic of designing new hybrid sequences, made of peptides and peptoids (12), class of oligomers recently driving widespread interest, amenable of easy functionalization with bioactive motifs at their side-chains. Another option for the functionalization of these SAPs was to add a cell adhesion motif like RGD (13) or IKVAV at the C-termini (peptides B18, B19, B52, B53, B54, 59) via a Gly-spacer. The importance of H-bond forming serines in self-assembling was assessed via their substitution with alanines (peptides B24, 30, B32, B33, B41, B42, B44, B46, B54, B55, B52, B50, B51, B57). Serines were also substituted with cystein in B47 and B48.

Peptides total net charge at neutral pH was changed by substituting a serine 8 with glutamic Acid (B17) or by replacing lysine with opposite charged residues (B10 and B12) or, alternatively, neutral residues (B11, B13 and B43). Lysine was also replaced with positively charged arginine (B22). Phenylalanine was substituted with tryptophane (B27, B32), with tyrosine (B39) or with alanine (B40). The G-spacer length was varied (between the N-termini and the BMHP fragment) from 0 (Biot-PFSSTKT-CONH2) to 1 (B29, B50), to 3 (peptide B3) and 5 residues (peptides B25 and B51). While in case of the first sequence no self-assembling was detected at both nano- and mesoscales, that was not the case for peptides B3, B25, B29, B50 and B51. A branched peptide (B58) was introduced to act as knot between assembled nanostructure thus altering the biomechanical properties of the other hydrogels when dissolved with any of the other linear peptides. Lysine was shifted in different position within the sequence (B64, B65, B66, B67)

Some of the proposed modifications were combined together to assess their synergistic effect, if any.

Example 2

Rheological Tests

Rheological properties were determined for the peptides of the invention, using a controlled stress TA Instruments AR-2000ex rheometer (TAInstruments). A cone-and-plate geometry (acrylic cone diameter, 20 mm; angle, 1°; truncation gap 34 µm) was used. All measurements were obtained at a constant monitored temperature of 25° C. Preliminary strain sweeps were performed for each sample to define the linear viscoelastic region, thus ensuring that moduli were independent of strain. Time sweeps, after addition of PBS (1×) were recorded at constant angular frequency ($\omega$=1 Hz). Frequency sweeps, both for peptide water solutions and for self-assembled scaffolds, were performed with the instrument in oscillatory mode at controlled strain of 1%. Final: onset point of rupture was calculated by linear interpolation and subsequent determination of the intersection of the G' modes in the linear region and at material rupture respectively. G' values were averaged in the 1-100 Hz region and between n=3 independent replicates. During self-healing tests the self-assembled scaffold was torn by applying a strain sweep (0.01%-1000% strain range) at 1 Hz oscillatory frequency. G' values were is recorded in frequency sweep mode (at 1% strain) or, in time sweep mode (at 1 Hz and at 1% strain), before and after the strain sweep step, subsequent observations were performed every half hour or, in case of time sweep test, every 30 seconds. Values for all peptides, averaged in the 1-100 Hz range, are reported in FIG. 2d. In all of the SAPs the difference between the storage moduli measured before and after PBS addition spanned from two to four orders of magnitude, proving the dramatic biomechanical changes taking place during scaffold gelation. Peptide B3 (1%) yielded a solid stiff scaffold (G'=2917 Pa), supporting the idea that ionic charges may screen the electrostatic repulsions given by positively charged lysine residues and speed up the spontaneous ongoing self-assembling process, on its turn giving an already viscous (G'=67 Pa) and opaque solution at day 1. Among the peptides giving soft scaffold (100 Pa-1000 Pa range) peptides 4, B19, B25, B28 and 30 were included. On the opposite side, SAPs yielding solid stiff scaffolds are B15, B22, B24, B27 and 31 (5000 Pa-9000 Pa range).

Additionally, in case of B15, Proline substitution did produce a stiff solid scaffold (G'=8500 Pa) while for B24, the simultaneous substitution of proline and serine 7, the latter important in self-assembling for its role in H-bonds formation, with a couple of alanines, brought the overall scaffold stiffness to values higher (G'=6502 Pa) than peptide B3. On the other side, proline substitution with a peptoid residue (B28) decreased the assembled scaffold stiffness and increased the minimum necessary peptide concentration for gelation (namely 3% w/v).

G-spacer variations affected the final scaffold stiffness (B25), while its absence prevented the tested peptide from forming any scaffolds.

Biotin substitution with tryptophan (peptides 4 and 30) dramatically decreased G' (if compared to B3 and B24 respectively) and the rate of the viscosity increments of the peptide solution before pH shift. Biotin deletion prevented any scaffold formation instead (peptide 2).

Macro-Scale Characterization of the Peptides of the Invention and Rheology

All of the synthesized peptides are soluble at 1% w/v concentration in distilled water and in acid (0.1 M HCl) solutions. Peptides B10, B11, B12 and B13, are immediately self-assembling with dissolution in water.

Figure 2A:
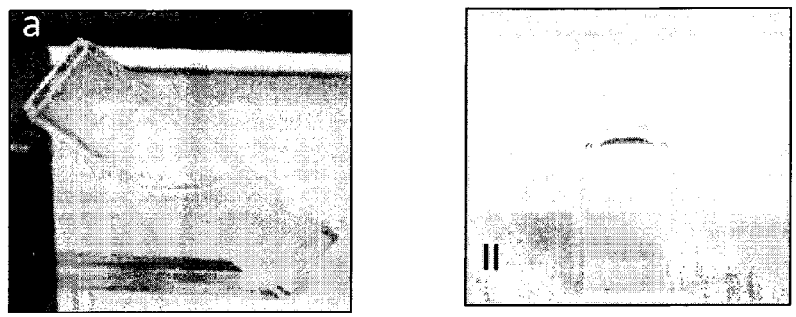
FIG. 2 shows a gelation experiment of the self-assembling peptides in which solution G' kinetic dependency on peptide concentration is shown.
FIG. 2b: storage modulus (G') of peptide B3 dissolved at 3% concentration reaches a plateau after 2 days (variation of 7% between day 2 and day 5), while G' still importantly increases at day 5 in the case of a 2% solution.
FIG. 2c: typical measurements of storage (G') and loss (G") moduli of assembled scaffolds after pH shift (peptides 4, B15, B22) and as a control the still liquid solution of the non-assembling peptide B7 (Biot-PFSSTKT-$CONH_2$)
FIG. 2d shows identification numbers and the corresponding SEQ ID NO., sequences and average values of the storage moduli, for the tested peptides, of peptide solutions (G' pre-assembling) and jellified scaffolds (G' post-assembling).

The tested peptides solutions appearance ranged from peptides giving clear liquid is solutions (e.g. 4, B15, B19, B25, B28, 30) to samples which become opaque in 1 to 7 days after dissolution (e.g. B3, B17, B22, B24, B27, 31) as shown in FIG. 2a (I). Most of the liquid solutions increased in viscosity over the first week after dissolution, however after ten days in water no appreciable changes happened at the macroscale. Upon exposure to PBS (1×) the following peptides yielded solid scaffolds similarly to FIG. 2a (II): B3, 4, B15, B17, B19, B22, B24, B25, B27, B28, 30, 31, B32, B33, B34, 37, B39, B40, B41, B42, B43, B44, B45, B46, B47, B48, B50, B51, B52, B53, B54, B57, B58, 59, 60, 61, B64 and B65 (black font in FIG. 1).

Figure 2B:
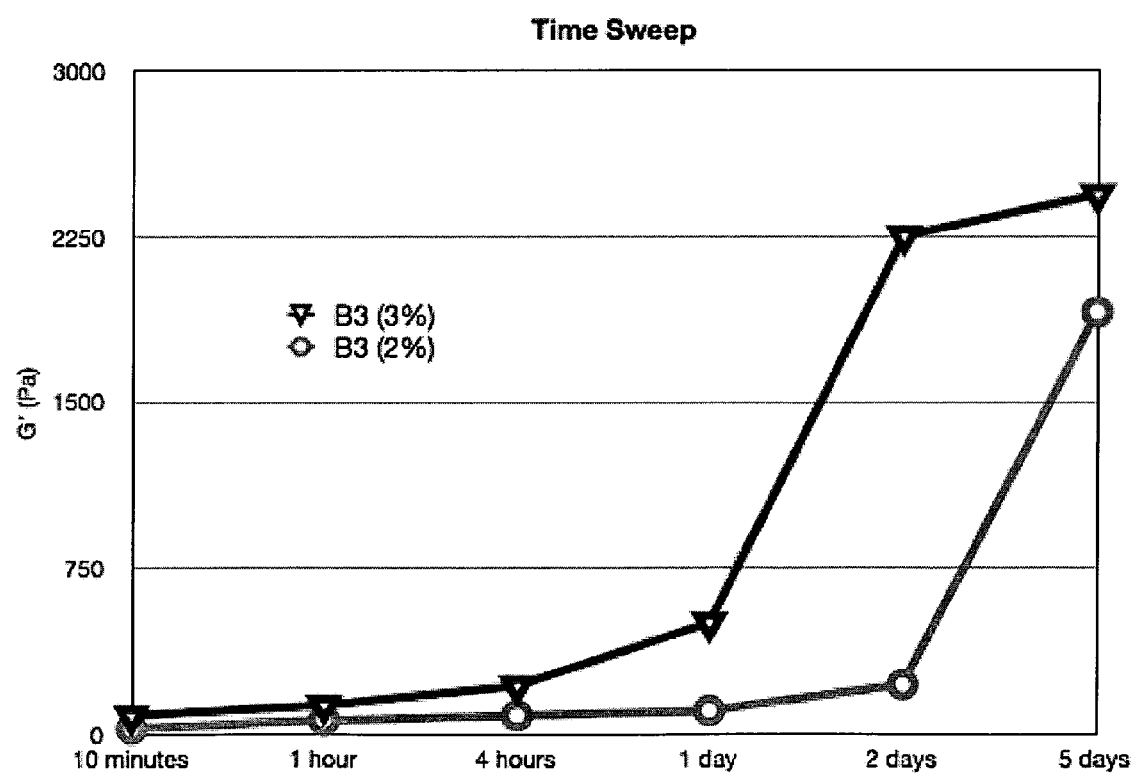

The mechanical properties of the synthesized peptides were tested with a cone-and-plate rheometer. Firstly, the G' dependence of peptide water solutions on concentration increments, and consequently aggregation kinetics, was assessed as shown in FIG. 2b. Clearly peptide B3 shows different mean G' values (averaged in the 1-60 Hz frequency range) starting from the day of dissolution (day 0) and reaching a plateau at day 2 for 3% concentration and still increasing at day 5 when dissolved at 2% concentration. This shows that rate of storage moduli increments increases along with peptide concentration.

Nonetheless, keeping constant the observation time, the storage moduli of peptide solutions previously dissolved (the day before) at 3% w/v were measured. Measurements were obtained of these peptide solutions, further diluted to 1% w/v at the same day of the experiment (unless otherwise specified), and, after addition of PBS, of the formed scaffolds. When the proposed standard conditions were not optimal for some of such heterogeneous ensemble of SAPs possessing different kinetics of self-assembling, (e.g. too viscous solutions for reliable user handling or poor scaffold gelation), it was chosen to increase the peptide concentration (B19, B28, 30 and 31) or to wait for more time for the spontaneous self-assembling to take place (4, B27 and 30) before triggering scaffold formation by varying the pH, or, conversely, to lower down the concentration (B3, B22 and B24) because of the hardly reproducible handling by the user of too highly viscous solutions.

For B10, B11, B12 and B13, yielding solutions of interspersed fragments of self-assembled scaffolds, measurements were unreliable and not reported.

Control peptide B7, having the amino acid sequence: Biot-PFSSTKT-CONH2, did is not give a solid scaffold at the macro-scale observations and did not show any steady G' increase after addition of neutral pH buffer in FIG. 2c) and was characterized by very low and not linear G' and G" values. As to the other peptides a stable linear frequency response (in the 1-100 Hz range) was detected, with G' values (representing the elastic character of the materials) well above G" values (representing the viscous character of the materials): hence resembling the typical responses of solid structures (see FIG. 2c).

Example 3

Atomic Force Microscopy

Each peptide of the present invention was analysed by Atomic Force Microscopy. Peptides were dissolved in distilled water (GIBCO), at a concentration of 3% w/v one day prior imaging. Imaging and measurements were collected at day 1, day 3, day 7 and so on (maximum observation time was 30 days after dissolution). The same day of imaging peptide solutions were diluted (in a ratio of 1 to 3 or more if fiber density was too high), 2 μl of these solutions were placed on mica muscovite substrates and kept at room temperature for 2 minutes. The mica surfaces were then rinsed with distilled water to remove loosely bound peptides and solution was let to evaporate for 30 minutes. AFM images were collected in Tapping™ mode by a MultiMode Nanoscope IIIa (Digital Instruments) using single-beam silicon cantilever probes (Veeco RTESP: resonance frequency 300 KHz, nominal tip radius of curvature 10 nm, forces constant 40 N/m). If necessary, images (1024×1024 resolution) were subjected to flattening. When tabular nanofibers were detected and fiber height was between 1 and 1.5 nm, i.e. far lower than the tip radius (10 nm), tip convolution effect was corrected with the formula:

$$\Delta x = \sqrt{2[h(2r_t - h)]} \quad (1)$$

Where Δx is the width broadening effect, h is the nanofiber height, and rt is for tip radius.

Results are presented as means averaged over more than 100 measurements.

Atomic Force Microscope (AFM) Imaging and Characterization of the Peptides of is the Invention.

Deep characterization of the spontaneous self-assembly at the nano- and microscale required imaging with AFM of all of the synthesized peptides. The self-assembling peptides gave rise to various structures that could be grouped in six categories as represented in FIG. 3.

Self-assembling peptides B64, B65, B66 and B67 formed twisted nanofiber formations (60 nm pitch, left-handed) since 1 day post dissolution, and also self-assembled giving a hydrogel upon exposure to PBS (FIG. 3a).

Proline-free peptides B15, B24, B32, B33, B40, B41, B42, B54, B58, 59, B44 and 61 gave rise to tabular long fibers (ranging from 5 μm to 10 μm in length). Nanofiber heights were of 1.6 nm and multiples, while widths were of 8-9 nm and multiples, given by fibers clamped together laterally (FIG. 3b). Average fiber dimensions did not change significantly at the tested time-points (up to 10 days after dissolution).

In case of peptide 4, 37 and 60 thicker fibers (minimum width of 30 nm), likely made of coiled thinner intermediate filaments similar to those imaged with B15 and B24, were imaged. Moreover, mostly twisted fibers were present (see FIG. 3c), showing a left-handed pitch ranging from 100 to 150 nm (measured as top-to-top horizontal distances). Heights were of 2.5 nm and multiples (measured at the slope bottoms), with a vertical span of 5 nm (registered as a top-to-bottom vertical distance) in the profile shape of the same twisted fiber. Notably, at the selected observation time points of day 1, 3 and 10 the density of imaged fibers (i.e. number of fibers per imaged field) increased over time, consistently with the previously observed slow kinetic of viscosity increments of peptide 4.

Similar fibers but with different features were seen for peptides B18, B19, B25, B28, B29, 30, 31, B45, B50, B51, B52 and B53 (FIG. 2e). In this set of peptides the twisted fiber width was 15 nm and 30 nm while heights could be grouped in 6 nm (bottom)-11 nm (top) and 12 nm (bottom)-19 nm (top), giving an approximate vertical span of 6 nm between top and bottom fibers (only 2 nm in the case of 30). Pitches of the left-handed twisted fibers measured between 80 nm and 110 nm, except for B28 (whose fiber pitches ranged from 30 nm to 40 nm). In the case of peptide B25 side-by-side packed fibers were occasionally seen, however this fact might be just a side effect of the sample prepared through water evaporation. In the first days after dissolution B19 also formed flat intermediate-fibers that eventually wrapped in the days after. For peptide 31 intermediate-fibers (height: 3.6 nm to 4.3 nm; pitch: 35 nm) gradually packed together giving similar eventual nanofibers.

Necessarily, peptides B10, B11, B12, B13 and B43 were grouped together because of the poor handling which, at least, allowed for imaging of some scattered chunks of aggregated left-handed twisted fibers, as can be seen in FIG. 3d. In this case the immediate self-assembling, given by the neutral or negative total net charge, immediately caused filaments to bundle together, lowering down their potential for making solid scaffolds.

In the last group intermediate left-handed twisted protofibrils (FIG. 3f(I); width 8.5 nm and multiples; height 2-2.8 nm; 28-30 nm pitch for B3 and B22, 90-110 nm for B17 and B27) of peptides B3, B17, B2, B27, B34, B39, B46, B47, B48 and B57 aligned side-by-side and hierarchically self-organized in bigger ribbon-like long structures (featuring highly variable pitches and more than 12 μm long structures) (FIG. 3f(II)) characterized by both left and right turns, that, on their turn, helically coil to form straight tubular structures (FIG. 3f(III)) and eventually double- or multi-layered flat sheets (FIG. 3f(IV)), giving structures as high as 3-3.6 nm (3f(III)) and 6.4 or 14 nm (3f(IV)) respectively. Particularly in the last group the kinetic of the hierarchically self-assembling was clearly detectable up to 10 days following dissolution (smaller protofibrils were followed by bigger ribbons, tubular structures and flat sheets): after that time growing microstructures, as big as several squared microns, are affected by sample preparation thus not discussed here.

The members of this last group of SAPs all share the presence of biotin, the triplet of glycines, proline 5 except for the B57 peptide, an aromatic residue at position 6, serine 7 or serine 8 (except for B57) and a positively charged residue at position 10 (or 8 for B57). Thus, in general, the following generic sequence, bio-GGG-PX$_1$SXxXxX$_3$Xx, (where X$_1$=aromatic residue; Xx=h-bond forming residues; X$_3$=positively charged residue) can actually self-assemble at multiple levels of arrangements hierarchically. Other substitutions with similar residues will be required to highlight more generic specification to this type of self-assembling to take place.

The dipeptide Phe-Phe forms tubular structures, which directly indicated the importance of the aromatic interaction for structure formation (14), and the self-assembled ultra-structure dependence of tetrapeptides on the relative positions of proline and phenylalanine residues, suggesting a crucial role of pyrrolidine-aromatic and π-π interactions in fiber formation.

Example 4

X-Ray Diffraction Analysis (XRD)

Each peptide of the present invention was analysed with X-ray diffraction.

X-ray diffraction data were collected at a multiple-wavelength anomalous diffraction and monochromatic macromolecular crystallography beamline 8.3.1, at the Advanced Light Source located at Lawrence Berkeley National Laboratory. Beamline 8.3.1 has a 5 tesla single pole superbend source with an energy range of 2.4-18 keV. Data were collected with a 3×3 CCD array (ADSC Q315r) detector at a wavelength of 1.1159 Å. Data sets were collected at 200-mm distances with 40 s exposure times and 1 degree oscillations on a bulk sample of SAPs dissolved the day before at 3% w/v concentration. In case of partially soluble peptides higher concentrations were adopted and the insoluble samples were discarded. Peptide fiber containing solutions were centrifuged at 12,000 rpm for 10 minutes. The resulting concentrated solution was then dropped on a 0.2-0.3 mm diameter nylon loop. Data were processed in Igor Pro 6.0 with a silver behenate (AgBE) standard.

Circular Dichroism (CD) Analysis

Far-UV CD spectra of each of the peptides of the present invention are recorded between 190 nm-260 nm at room temperature on an Aviv 62DS spectrometer. All measurements were carried out in 1-mm quartz cuvette in distilled water. Spectra are from accumulation of 3 scans. Blank spectra of the buffer without sample are subtracted. CD spectra of peptide samples at 0.02%, 0.04% and 0.06% w/v concentrations are collected at one day after dissolution in water. Spectra are recorded in 2-nm steps, averaged over 4 seconds and normalized into Delta Epsilon units. Protein structures were deconvoluted by using the CD Spectra Deconvolution Software 2.1 using 33 base spectra of known proteins.

X-Ray Diffraction (XRD) Data and CD Characterization of the Peptides of the Invention The following peptides were tested for XRD studies: B3, 4, B12, B13, B15, and B19, B25, B33, B34, B47, B48, B53. Measurements were taken of samples dissolved the day before the experiments at 3% concentration. Most of the tested peptides gave isotropic rings with the maximum intensity at approximately 4.7 Å distance, usually ascribed to the h-bonding spacing between β-strands, typical of unaligned β-sheet forming fibers (see FIG. 4a). Another clearly visible ring was found at 3-1.7 nm distance interval. Additionally, radial integration of the patterns revealed other diffraction peaks (FIG. 4b), shared by all peptides, at 3.7-3.8 Å, typical van der Waals distance of packed peptide side-chains, and 2.3-2.4 Å, considered as the second order of the 4.7 Å peak. Nonetheless these maxima gave a much less intense signal if compared to the 4.7 Å peak.

Notably, B3, B12, B13, B34, B47, B53 peptides showed a medium intensity peak at 2.1 nm (arrow in FIG. 5a), while peptides B19 and 4 gave a peak at 2.86 nm and 2.35 nm respectively. In B15, B33, B48 the maxima was detected at 1.73 nm. In B25 we had a peak at 1.96 nm. Beside B19, for whom likely protofibrils were simply not detected, and B12 and B13, where reliable AFM measurements could not be obtained, the peaks at distance greater than 1.5 nm were consistent with nanofiber heights measured via AFM. Different heights resembled different molecular arrangements giving twisted or tabular fibers, or, at the higher level of self-organization, ribbon-like tubular structures. Lastly peaks at 5.2 Å, like in B3, or, in general, between 5 Å and 8 Å, for peptides B12, B13, B15, B19, B25, B33, B34, B47, B48 and B53 may be interpreted as inter-molecular aromatic interactions: interactions not seen in the case of biotin substitution with tryptophane in peptide 4.

Circular Dichroism (CD) spectroscopy studies were run to asses the secondary structures, spontaneously formed by the following self-assembling peptides: B3, 4, B15, B17, B19, B22, B24, B25 B27, B28, 31, 30, B33. All of the tested peptides dissolved in pure water showed spectra (similar to that one depicted in FIG. 4b for peptide B24), that, once deconvolved, gave more than 50% presence of β-structures, thus supporting the previous interpretation of the 4.7 Å distance.

Example 5

In Vitro Tests

Neural Stem Cells Seeding and Imaging

Neural precursor cultures are established and expanded as previously described (15, 16). Human neural stem cells (NSCs) were isolated from the central nervous system, in particular from the diencephalon and the cerebral cortex of human brain 10.5 weeks from conception. The modalities for obtaining the primary tissue are in agreement with the guidelines of the European Network for Transplantation (NECTAR).

In vitro tests were performed following a previously adopted methodology (5). Briefly, cells (at a concentration of $6 \times 10^4$ cells/cm$^2$) were seeded on the top-surface of each assembled scaffold previously assembled into 96 multiwells. Initially, cells were cultured with basal medium supplemented with βFGF (10 ng/ml), added to enhance neuronal progeny differentiation. At 3 days in vitro (DIV), βFGF medium was replaced with Leukemia Inhibitory Factor (LIF, Chemicon) (20 ng/ml) and Brain Derived Neurotrophic Factor (BDNF, Peprotech) (20 ng/ml). Fresh medium was added every three days. Positive and negative controls consisted of CULTREX-BME® substrate (R&D systems) (1:100 dilution in basal medium) and untreated bottom well surfaces respectively.

Live/Dead cell imaging (MolecularProbes) was obtained by incubating cells cultured for 10 days with a staining solution containing 2.0 μM calcein AM and 4.0 μM ethidium homodimer in PBS at 37° C. for 60 min and visualized by inverted fluorescence microscope (Zeiss).

Cell viability was quantified via CELLTITER 96® Aqueous Proliferation Assay (Promega, Madison, Wis.) at 7 DIV as recommended in the Promega protocol. After calibrating the linear response between the cell number and absorbance values, proliferated cell populations were quantified (n=6) by using a Vmax microplate reader (Molecular Devices, Sunnyvale, Calif.) at 490 nm wavelength. Values, reported as means±standard error of the mean, were blanked to their respective controls consisting of same substrates and cell culture media without cells.

To assess the differentiated phenotypes cells were stained at 14 DIV for βIIITubulin (Covance, 1:750), GFAP (Chemicon, 1:3000), MAP2 (Sigma, 1:200), GalC (Chemicon, 1:200) and O$_4$ (Chemicon, 1:200), subsequently marked with Cy3 (Jackson, 1:1000) and Alexa 488 (Molecular Probes, 1:1000) secondary is antibodies. In details, cells were fixed in paraformaldehyde 4% for 15 minutes, permeabilized 10 minutes with PBS/0.1% Triton X-100 and blocked for 1 hour with PBS/20% Normal Goat Serum. Samples were incubated overnight in PBS/10% Normal Goat Serum solutions of primary antibodies and incubated overnight at +4° C. After several washes with PBS, secondary antibodies diluted in PBS/10% Normal Goat Serum were applied for 1 hour. Cell nuclei were counterstained with DAPI, samples were mounted with FluorSave reagent (Calbiochem) and samples were visualized and analyzed with a fluorescence microscope. βIIITubulin$^+$, GFAP$^+$, GalC$^+$/O$_4^+$ and MAP2$^+$ cells were quantified by counting positive cells in 4 independent experiments Scaffolds for In Vitro Cell Cultures To assess the potential of the proposed SAPs for cell cultures and, more generally, for regenerative medicine, a two-dimensional cell culture protocol already developed for RADA16-I-like peptides was adapted (5). Briefly, human Neural Stem Cells (hNSCs), mechanically dissociated 1 day before plating, were seeded and cultured for one week in vitro over self-assembled scaffolds of B3, 4, B15, B17, B19, B22, B24, B25, B27, B28, 30, 31 and over non-coated tissue culture plastic wells (negative control). Phase contrast imaging revealed an heterogeneous degree of spreading of cultured hNSCs over the various peptides (see FIG. 5a), ranging from proliferated cell clusters (in case of B17, B22 and B28), to branched cells (B3, B15 and 31) to adhered and differentiating hNSCs (B24).

Imaging of calcein-AM-labeled living cells and ethidium-homodimer-labeled dead cells cultured for 10 days showed highly viable cells clustered in round-shaped clusters in case of plastic (FIG. 5b), clamped in poorly branched aggregates (B22) or distributed throughout the gel top surface (B24). The negligible percentage of dead cells (red dots) seems to refute a possible cytotoxic effect of these materials.

CellTiter assay results, resumed in FIG. 5c, showed that most of the substrates improved hNSC viability when compared to negative control. In particular, B24 showed the highest values of viable NSCs at 7 DIV, while in differentiation experiments at 14 DIV, the percentages of $\beta$IIITubulin$^+$, MAP2$^+$, GalC/O4$^+$ and is GFAP$^+$ cells (FIG. 5d) were comparable to standard hNSC differentiation data obtained with animal extracts (5).

In most of the self-assembled scaffolds the original BMHP sequence, already proved to stimulate hNSC proliferation and differentiation (5), is here likely not fully exposed or modified in the crucial residues (B17, B22, B25, B27, 30) for cell membrane receptor binding: in particular in B3, B17, B22 and B27 hierarchical aggregation may 'bury' the PFSSTKT-like motif within complex structures impairing the correct exposure of whole active sequence. This is not the case of B24 and B15, where the tabular structure of $\beta$-sheet nanofibers probably allows a better solvent exposure of the functional motifs.

Biotin-free peptides 4 and 31 produced results comparable to the biotinilated peptides.

The addition of the RGD motif adopted in B19 can be considered as the proof-of-concept, giving results significantly different from negative control (P<0.002: paired t-test), that, with the specific set of selected residues, these SAPs may be effectively functionalized without preventing peptide self-assembling.

B28 achieved a cell population comparable to those of the other peptides regardless of its partially unnatural sequence.

B24 supported hNSCs differentiation toward neurons ($\beta$IITubulin and MAP2 markers), astrocytes (GFAP marker) and oligodendrocytes (GalC/O$_4$ markers), the three main cell phenotypes of the central nervous system.

Taken together these results demonstrate that these SAPs can foster hNSC survival, spreading and differentiation: quality that increases their potential as tool for 2D and 3D cell cultures and regenerative medicine.

Example 6

Self-Healing Materials

Interestingly, most of the self-assembling peptides were also verified for their self-healing propensity, namely, the capability of switching back to fully formed hydrogels with viscoelastic properties similar to that of the pre-strained assembled gel. Solid scaffolds were obtained via addition of PBS (1×) in a cone-and-plate rheometer; we measured the storage modulus, the samples were subjected to a strain sweep (0.01% to 1000%) until and far beyond rupture occurred (i.e. is monitoring the sudden drop of G' value). Samples were then left in place (keeping them hydrated with PBS) and their G' were measured every 30 minutes via frequency sweep tests in the range of 0.1 Hz to 60 Hz. As a negative control KLD-12, a well-known SAP, was tested (4, 6). For peptides B17 (1% w/v/concentration) a gradual increase was detected, till full recovery, of the initial G' values at 120' after rupture as can be seen in FIG. 6a, while, in case of KLD-12, storage moduli values were similar to those registered immediately after breakage (FIG. 6c). In FIG. 6b peptide B25 (3% w/v concentration) was assessed for self-healing in a time sweep mode, every 30 seconds, at 1 Hz and at 1% strain. Values of G' recovered after 100 minutes (1000 Pa) and steadily plateaued over time. For peptides B3, B22, B25 and B27 full recovery was obtained at different time intervals after rupture, ranging from 60' to 240'. Similar results were confirmed by multiple independent experiments, but at different time ranges, for all of the self-assembling peptides except for B19 and B28.

Additionally, multiple and consecutive mechanical breakages were obtained by stirring the scaffolds, previously self-assembled in transparent cuvettes (as seen in FIG. 2a), via pipette tips and subsequent vortexing. Samples were checked for rupture by tilting. After a maximum of four hours all of the samples returned to their solidified gel appearance. This healing could be repeated at will.

It must be stated that the self-healing phenomenon is probably a re-arrangement, at the meso-scale, of the high-level aggregated structures (sheets and ribbon-like structures): the smaller proto-fibrillary structures seen at the high magnification imaging at AFM are preserved in these tests. Scaffolds coming from the above mentioned peptides are likely formed by transient physical cross-links that form between assembled nanostructures at the higher level of the hierarchically self-aggregation, i.e. among straight tubular fibers and sheets.

Example 7

Scaffolds for Tissue Engineering Applications

To test if the SAPs according to the present invention show any toxicity when used in vivo we assessed the tissue reaction to multiple injections of B24 into the spinal cord of rats. All procedures involving animals were performed according to EC guidelines (EC Council Directive 86/609, 1987), to the Italian legislation on animal is experimentation (Decreto L. vo 116/92) and to protocols approved by the Animal Care and Use Committee of the University of Milan-Bicocca (IACUC 37/07).

Female Sprague-Dawley rats weighting 200-250 gr (Charles River Laboratories) were divided into two groups: 1) animals receiving injections of saline solution (control group, n=3) and 2) animals treated with B24 (n=3). In the case of long term observations (1 month) similar injections of B24 were used (n=2). Rats were anesthetized with an intraperitoneal injection of ketamine (80 mg/kg) and xylazine (10 mg/kg). The spinal cord was exposed at the T9-T10 level, and, after laminectomy, animals were injected with B24 (1% aqueous solution) or saline solution using a Hamilton syringe held via a micromanipulator. The solutions were delivered at distances of 500 µm, and two injections of 0.5 µl each were made at each interval, for a total dose of 3 µl. After injection, the muscles were sutured and the skin was closed with wound clips. Rats were treated daily with analgesic (carprofen, 5 mg/kg) and antibiotic (enrofloxacin, 5 mg/kg). 3 days after surgery (for toxicity tests) or 1 month after surgery (nervous regeneration tests) animals were sacrificed by transcardial perfusion with 4% paraformaldehyde. Spinal cords were removed, embedded in OCT, frozen and sliced into 16 μm thick longitudinal sections. For immunofluorescence analysis slices were permeabilized and blocked with PBS/0.3% TritonX-100/10% Normal Goat Serum (NGS) for 1 hour at room temperature. Then slices were incubated 16 hours with the following primary antibodies diluted in PBS/0.3% TritonX-100/1% NGS: anti-CD68 (1:500, Serotec), anti-βIIITubulin (1:400, Covance), anti-growth associated protein 43 (GAP-43) (1:200, Millipore) and anti-SMI 32 (1:1000, Covance). Goat anti Mouse Alexa 488 (Molecular Probes; 1:1000) and anti-rabbit Cy3 (Jackson, 1:1000) secondary antibodies diluted in PBS/0.3% TritonX-100/1% NGS were used for signal detection by incubating slices for 1 hour. Cell nuclei were counterstained with DAPI (Roche) and slices were mounted with Fluorsave (Calbiochem). For short-term histochemical analysis, slices were stained with hematoxylin/eosin. Tunel assay was performed using the In Situ Cell Death Detection Kit (Roche) according to the manufacturer's instructions. Images were taken with Zeiss Apotome Observer Z.1.

For each staining analyses were performed on six contiguous slices of the is injection sites per each animal.

Strikingly B24 prevented the hematoma physiologically forming after micro-injections found in control group (FIGS. 7F,G and 7A,B respectively). Three days after injection, the spinal cord tissue of B24-injected animals displayed a negligible number of infiltrated macrophages and apoptotic cells in and around the area of the injections (FIG. 7H,I respectively) if compared to saline-injected animals (FIG. 7C,D respectively). The neurofilament H dephosphorilated nervous fibers were equally present in saline-injected and in B24-treated animals (FIG. 7E,J). Summarizing, B24 prevented hematoma formation due to experimental surgery, it did not enhance either significant macrophages infiltration or apoptotic cell death and did not exacerbate nervous fibers degeneration when compared to saline-injected animals.

At one month after injections, the scaffold made of B24 did not exert any chronic inflammation in the spinal cord: on the contrary, it has been widely invaded by regenerating nervous fibers (FIG. 8a) positive to βIIITubulin and GAP-43 neuronal markers. In particular, bundles of newly formed axons infiltrated the inner portion of the implanted scaffold (FIG. 8b).

Taken together these results evince an appreciable in vivo biocompatibility of the tested peptides, and their potential as scaffolds for nervous regenerative applications.

The novel self-assembling peptides according to the present invention and made according to Examples 1-7 form tabular nanofibres which surprisingly self assemble into complex interwoven membranes of a few microns in width in mild conditions. Interestingly such novel peptides also have self-healing properties and can be used for different applications such as scaffolds for in vitro cell culture and tissue regeneration, drug delivery, hemostatic compounds and other non-medical applications such as molecular switches and pH sensitive devices.

From the above description and the above-noted Examples, the advantages attained by the product described and obtained according to the present invention are apparent.

REFERENCES

1. Tibbitt, M. W. & Anseth, K. S. Hydrogels as extracellular matrix mimics for 3D cell culture. Biotechnol Bioeng 103, 655-663 (2009).
2. Hamidi, M., Azadi, A. & Rafiei, P. Hydrogel nanoparticles in drug delivery. Adv Drug Deliv Rev 60, 1638-1649 (2008).
3. Nisbet, D. R., Crompton, K. E., Horne, M. K., Finkelstein, D. I. & Forsythe, J. S. Neural tissue engineering of the CNS using hydrogels. J Biomed Mater Res B Appl Biomater 87, 251-263 (2008).
4. Kisiday, J. et al. Self-assembling peptide hydrogel fosters chondrocyte extracellular matrix production and cell division: implications for cartilage tissue repair. Proc Natl Acad Sci USA 99, 9996-10001 (2002).
5. Gelain, F., Bottai, D., Vescovi, A. & Zhang, S. Designer self-assembling Peptide nanofiber scaffolds for adult mouse neural stem cell 3-dimensional cultures. PLoS ONE 1, e 119 (2006).
6. Zhang, S., Gelain, F. & Zhao, X. Designer self-assembling peptide nanofiber scaffolds for 3D tissue cell cultures. Semin Cancer Biol 15, 413-420 (2005).
7. Zhang, S., Holmes, T., Lockshin, C. & Rich, A. Spontaneous assembly of a self-complementary oligopeptide to form a stable macroscopic membrane. Proc Natl Acad Sci USA 90, 3334-3338 (1993).
8. Gazit, E. Self-assembled peptide nanostructures: the design of molecular building blocks and their technological utilization. Chem Soc Rev 36, 1263-1269 (2007).
9. Taraballi, F. et al. Effect of functionalization on the self-assembling propensity of beta-sheet forming peptides. Soft Matter 5, 660-668 (2009).
10. Jitrapakdee, S. & Wallace, J. C. The biotin enzyme family: conserved structural motifs and domain rearrangements. Curr Protein Pept Sci 4, 217-229 (2003).
11. Lei, Y., Li, H., Zhang, R. & Han, S. Theoretical study of cooperativity in biotin. J Phys Chem B 111, 14370-14377 (2007).
12. Zuckermann, R. N. & Kodadek, T. Peptoids as potential therapeutics. Curr Opin Mol Ther 11, 299-307 (2009).
13. D'Souza, S. E., Ginsberg, M. H. & Plow, E. F. Arginyl-glycyl-aspartic acid (RGD): a cell adhesion motif. Trends Biochem Sci 16, 246-250 (1991).
14. Reches, M. & Gazit, E. Casting metal nanowires within discrete self-assembled peptide nanotubes. Science (New York, N.Y. 300, 625-627 (2003).
15. Vescovi, A. L., Reynolds, B. A., Fraser, D. D. & Weiss, S. bFGF regulates the proliferative fate of unipotent (neuronal) and bipotent (neuronal/astroglial) EGF-generated CNS progenitor cells. Neuron 11, 951-966 (1993).
16. Vescovi, A. L. et al. Isolation and cloning of multipotential stem cells from the embryonic human CNS and establishment of transplantable human neural stem cell lines by epigenetic stimulation. Exp Neurol 156, 71-83 (1999).

The invention claimed is:

1. An isolated self-assembling peptide (SAP) comprising the amino acid sequence of SEQ ID NO: 31.

2. The self-assembling peptide according to claim 1, wherein the N-terminus of the self-assembling peptide is optionally biotinylated.

3. The self-assembling peptide according to claim 1, wherein the N-terminus of the self-assembling peptide is optionally acetylated.

4. A hydrogel, comprising the self-assembling peptide according to claim 1 and a hydrogelating ingredient.

5. An isolated self-assembling peptide polymer, wherein the polymer comprises at least two self-assembling peptides according to claim 1.

6. A tabular nanofiber, wherein the tubular nanofiber comprises at least two self-assembling peptides according to claim 1.

7. The tabular nanofiber according to claim 6, wherein the tubular nanofiber is from 5 μm to 10 μm in length.

8. A complex interwoven membrane, wherein the membrane comprises at least 2 tabular nanofibers according to claim 6.

9. The complex interwoven membrane according to claim 8, wherein the membrane is 0.5 μm to 4 μm wide.

10. A self-assembled nanostructure, wherein the nanostructure comprises of two or more self-assembling peptides according to claim 1.

11. The self-assembled nanostructure according to claim 10, wherein the nanostructure has a hollow cavity.

12. A method for using the self-assembled nanostructure according to claim 11 for the release of molecular drugs, comprising confining the molecular drugs in the hollow cavity of the nanostructure.

13. A method for using the hydrogel according to claim 4 as a scaffold for in vitro cell culture, comprising seeding the hydrogel of claim 4 with cells and culturing the cells with the hydrogel.

14. The method according to claim 13, wherein the hydrogel is capable of supporting an in vitro cell culture in two and three dimensions.

15. The method according to claim 13, wherein the hydrogel is capable of use as a scaffold for the in vitro growth and differentiation of human or murine neural stem cells.

* * * * *

SEQUENCE LISTING

<160> NUMBER OF SEQ ID NOS: 48

<210> SEQ ID NO 1
<211> LENGTH: 10

```
<212> TYPE: PRT
<213> ORGANISM: Artificial
<220> FEATURE:
<223> OTHER INFORMATION: Prepared by synthesis

<400> SEQUENCE: 1

Gly Gly Gly Pro Phe Ser Ser Thr Lys Thr
1               5                   10

<210> SEQ ID NO 2
<211> LENGTH: 11
<212> TYPE: PRT
<213> ORGANISM: Artificial
<220> FEATURE:
<223> OTHER INFORMATION: Prepared by synthesis

<400> SEQUENCE: 2

Trp Gly Gly Gly Pro Phe Ser Ser Thr Lys Thr
1               5                   10

<210> SEQ ID NO 3
<211> LENGTH: 10
<212> TYPE: PRT
<213> ORGANISM: Artificial
<220> FEATURE:
<223> OTHER INFORMATION: Prepared by synthesis

<400> SEQUENCE: 3

Gly Gly Gly Pro Phe Ser Ser Thr Asp Thr
1               5                   10

<210> SEQ ID NO 4
<211> LENGTH: 10
<212> TYPE: PRT
<213> ORGANISM: Artificial
<220> FEATURE:
<223> OTHER INFORMATION: Prepared by synthesis

<400> SEQUENCE: 4

Gly Gly Gly Pro Phe Ser Ser Thr Asn Thr
1               5                   10

<210> SEQ ID NO 5
<211> LENGTH: 10
<212> TYPE: PRT
<213> ORGANISM: Artificial
<220> FEATURE:
<223> OTHER INFORMATION: Prepared by synthesis

<400> SEQUENCE: 5

Gly Gly Gly Pro Phe Ser Ser Thr Glu Thr
1               5                   10

<210> SEQ ID NO 6
<211> LENGTH: 10
<212> TYPE: PRT
<213> ORGANISM: Artificial
<220> FEATURE:
<223> OTHER INFORMATION: Prepared by synthesis

<400> SEQUENCE: 6

Gly Gly Gly Pro Phe Ser Ser Thr Gln Thr
1               5                   10

<210> SEQ ID NO 7
<211> LENGTH: 10
<212> TYPE: PRT
<213> ORGANISM: Artificial
```

```
<220> FEATURE:
<223> OTHER INFORMATION: Prepared by synthesis

<400> SEQUENCE: 7

Gly Gly Gly Ala Phe Ser Ser Thr Lys Thr
1               5                   10

<210> SEQ ID NO 8
<211> LENGTH: 10
<212> TYPE: PRT
<213> ORGANISM: Artificial
<220> FEATURE:
<223> OTHER INFORMATION: Prepared by synthesis

<400> SEQUENCE: 8

Gly Gly Gly Pro Phe Ser Glu Thr Lys Thr
1               5                   10

<210> SEQ ID NO 9
<211> LENGTH: 14
<212> TYPE: PRT
<213> ORGANISM: Artificial
<220> FEATURE:
<223> OTHER INFORMATION: Prepared by synthesis

<400> SEQUENCE: 9

Gly Gly Gly Ala Phe Ser Ser Thr Lys Thr Gly Arg Gly Asp
1               5                   10

<210> SEQ ID NO 10
<211> LENGTH: 10
<212> TYPE: PRT
<213> ORGANISM: Artificial
<220> FEATURE:
<223> OTHER INFORMATION: Prepared by synthesis

<400> SEQUENCE: 10

Gly Gly Gly Pro Phe Ser Ser Thr Arg Thr
1               5                   10

<210> SEQ ID NO 11
<211> LENGTH: 10
<212> TYPE: PRT
<213> ORGANISM: Artificial
<220> FEATURE:
<223> OTHER INFORMATION: Prepared by synthesis

<400> SEQUENCE: 11

Gly Gly Gly Ala Phe Ala Ser Thr Lys Thr
1               5                   10

<210> SEQ ID NO 12
<211> LENGTH: 12
<212> TYPE: PRT
<213> ORGANISM: Artificial
<220> FEATURE:
<223> OTHER INFORMATION: Prepared by synthesis

<400> SEQUENCE: 12

Gly Gly Gly Gly Gly Pro Phe Ser Ser Thr Lys Thr
1               5                   10

<210> SEQ ID NO 13
<211> LENGTH: 10
<212> TYPE: PRT
<213> ORGANISM: Artificial
<220> FEATURE:
<223> OTHER INFORMATION: Prepared by synthesis
```

<400> SEQUENCE: 13

Gly Gly Gly Pro Trp Ser Ser Thr Lys Thr
1               5                   10

<210> SEQ ID NO 14
<211> LENGTH: 10
<212> TYPE: PRT
<213> ORGANISM: Artificial
<220> FEATURE:
<223> OTHER INFORMATION: Prepared by synthesis
<220> FEATURE:
<221> NAME/KEY: MISC_FEATURE
<222> LOCATION: (4)..(4)
<223> OTHER INFORMATION: Propylamine

<400> SEQUENCE: 14

Gly Gly Gly Xaa Phe Ser Ser Thr Lys Thr
1               5                   10

<210> SEQ ID NO 15
<211> LENGTH: 11
<212> TYPE: PRT
<213> ORGANISM: Artificial
<220> FEATURE:
<223> OTHER INFORMATION: Prepared by synthesis

<400> SEQUENCE: 15

Trp Gly Gly Gly Ala Phe Ala Ser Thr Lys Thr
1               5                   10

<210> SEQ ID NO 16
<211> LENGTH: 11
<212> TYPE: PRT
<213> ORGANISM: Artificial
<220> FEATURE:
<223> OTHER INFORMATION: Prepared by synthesis

<400> SEQUENCE: 16

Trp Gly Gly Gly Ala Phe Ser Ser Thr Lys Thr
1               5                   10

<210> SEQ ID NO 17
<211> LENGTH: 10
<212> TYPE: PRT
<213> ORGANISM: Artificial
<220> FEATURE:
<223> OTHER INFORMATION: Prepared by synthesis

<400> SEQUENCE: 17

Gly Gly Gly Lys Phe Ser Ser Thr Pro Thr
1               5                   10

<210> SEQ ID NO 18
<211> LENGTH: 10
<212> TYPE: PRT
<213> ORGANISM: Artificial
<220> FEATURE:
<223> OTHER INFORMATION: Prepared by synthesis

<400> SEQUENCE: 18

Gly Gly Gly Pro Lys Ser Ser Thr Phe Thr
1               5                   10

<210> SEQ ID NO 19
<211> LENGTH: 10
<212> TYPE: PRT
<213> ORGANISM: Artificial

```
<220> FEATURE:
<223> OTHER INFORMATION: Prepared by synthesis

<400> SEQUENCE: 19

Gly Gly Gly Pro Phe Ser Ser Lys Thr Thr
1               5                   10

<210> SEQ ID NO 20
<211> LENGTH: 10
<212> TYPE: PRT
<213> ORGANISM: Artificial
<220> FEATURE:
<223> OTHER INFORMATION: Prepared by synthesis

<400> SEQUENCE: 20

Gly Gly Gly Pro Phe Ser Ser Thr Thr Lys
1               5                   10

<210> SEQ ID NO 21
<211> LENGTH: 11
<212> TYPE: PRT
<213> ORGANISM: Artificial
<220> FEATURE:
<223> OTHER INFORMATION: Prepared by synthesis
<220> FEATURE:
<221> NAME/KEY: misc_feature
<222> LOCATION: (1)..(11)
<223> OTHER INFORMATION: Prepared by synthesis

<400> SEQUENCE: 21

Gly Gly Gly Gly Pro Phe Ser Ser Thr Lys Thr
1               5                   10

<210> SEQ ID NO 22
<211> LENGTH: 14
<212> TYPE: PRT
<213> ORGANISM: Artificial
<220> FEATURE:
<223> OTHER INFORMATION: Prepared by synthesis
<220> FEATURE:
<221> NAME/KEY: PEPTIDE
<222> LOCATION: (1)..(14)
<223> OTHER INFORMATION: Prepared by synthesis

<400> SEQUENCE: 22

Gly Gly Gly Pro Phe Ser Ser Thr Lys Thr Gly Arg Gly Asp
1               5                   10

<210> SEQ ID NO 23
<211> LENGTH: 8
<212> TYPE: PRT
<213> ORGANISM: Artificial
<220> FEATURE:
<223> OTHER INFORMATION: Prepared by synthesis

<400> SEQUENCE: 23

Gly Pro Phe Ser Ser Thr Lys Thr
1               5

<210> SEQ ID NO 24
<211> LENGTH: 10
<212> TYPE: PRT
<213> ORGANISM: Artificial
<220> FEATURE:
<223> OTHER INFORMATION: Prepared by synthesis

<400> SEQUENCE: 24

Gly Gly Gly Ala Trp Ala Ser Thr Lys Thr
1               5                   10
```

```
<210> SEQ ID NO 25
<211> LENGTH: 10
<212> TYPE: PRT
<213> ORGANISM: Artificial
<220> FEATURE:
<223> OTHER INFORMATION: Prepared by synthesis

<400> SEQUENCE: 25

Gly Gly Gly Ala Phe Ala Ser Thr Lys Ala
1               5                   10

<210> SEQ ID NO 26
<211> LENGTH: 11
<212> TYPE: PRT
<213> ORGANISM: Artificial
<220> FEATURE:
<223> OTHER INFORMATION: Prepared by synthesis

<400> SEQUENCE: 26

Gly Gly Gly Pro Phe Ser Ser Thr Lys Thr Pro
1               5                   10

<210> SEQ ID NO 27
<211> LENGTH: 11
<212> TYPE: PRT
<213> ORGANISM: Artificial
<220> FEATURE:
<223> OTHER INFORMATION: Prepared by synthesis

<400> SEQUENCE: 27

Phe Gly Gly Gly Pro Phe Ser Ser Thr Lys Thr
1               5                   10

<210> SEQ ID NO 28
<211> LENGTH: 10
<212> TYPE: PRT
<213> ORGANISM: Artificial
<220> FEATURE:
<223> OTHER INFORMATION: Prepared by synthesis

<400> SEQUENCE: 28

Gly Gly Gly Pro Tyr Ser Ser Thr Lys Thr
1               5                   10

<210> SEQ ID NO 29
<211> LENGTH: 10
<212> TYPE: PRT
<213> ORGANISM: Artificial
<220> FEATURE:
<223> OTHER INFORMATION: Prepared by synthesis

<400> SEQUENCE: 29

Gly Gly Gly Ala Ala Ser Ser Thr Lys Thr
1               5                   10

<210> SEQ ID NO 30
<211> LENGTH: 10
<212> TYPE: PRT
<213> ORGANISM: Artificial
<220> FEATURE:
<223> OTHER INFORMATION: Prepared by synthesis

<400> SEQUENCE: 30

Gly Gly Gly Ala Phe Ala Ala Thr Lys Thr
1               5                   10
```

```
<210> SEQ ID NO 31
<211> LENGTH: 10
<212> TYPE: PRT
<213> ORGANISM: Artificial
<220> FEATURE:
<223> OTHER INFORMATION: Prepared by synthesis

<400> SEQUENCE: 31

Gly Gly Gly Ala Phe Ala Ser Ala Lys Ala
1               5                   10

<210> SEQ ID NO 32
<211> LENGTH: 10
<212> TYPE: PRT
<213> ORGANISM: Artificial
<220> FEATURE:
<223> OTHER INFORMATION: Prepared by synthesis

<400> SEQUENCE: 32

Gly Gly Gly Pro Phe Ser Ser Thr Ala Thr
1               5                   10

<210> SEQ ID NO 33
<211> LENGTH: 10
<212> TYPE: PRT
<213> ORGANISM: Artificial
<220> FEATURE:
<223> OTHER INFORMATION: Prepared by synthesis

<400> SEQUENCE: 33

Gly Gly Gly Ala Phe Ala Ala Ala Lys Ala
1               5                   10

<210> SEQ ID NO 34
<211> LENGTH: 10
<212> TYPE: PRT
<213> ORGANISM: Artificial
<220> FEATURE:
<223> OTHER INFORMATION: Prepared by synthesis

<400> SEQUENCE: 34

Gly Gly Gly Pro Phe Ser Ser Ala Lys Thr
1               5                   10

<210> SEQ ID NO 35
<211> LENGTH: 10
<212> TYPE: PRT
<213> ORGANISM: Artificial
<220> FEATURE:
<223> OTHER INFORMATION: Prepared by synthesis

<400> SEQUENCE: 35

Gly Gly Gly Pro Phe Ser Ala Thr Lys Thr
1               5                   10

<210> SEQ ID NO 36
<211> LENGTH: 10
<212> TYPE: PRT
<213> ORGANISM: Artificial
<220> FEATURE:
<223> OTHER INFORMATION: Prepared by synthesis

<400> SEQUENCE: 36

Gly Gly Gly Pro Phe Ser Cys Thr Lys Thr
1               5                   10

<210> SEQ ID NO 37
<211> LENGTH: 10
```

```
<212> TYPE: PRT
<213> ORGANISM: Artificial
<220> FEATURE:
<223> OTHER INFORMATION: Prepared by synthesis

<400> SEQUENCE: 37

Gly Gly Gly Pro Phe Cys Ser Thr Lys Thr
1               5                   10

<210> SEQ ID NO 38
<211> LENGTH: 8
<212> TYPE: PRT
<213> ORGANISM: Artificial
<220> FEATURE:
<223> OTHER INFORMATION: Prepared by synthesis

<400> SEQUENCE: 38

Gly Ala Phe Ala Ser Thr Lys Thr
1               5

<210> SEQ ID NO 39
<211> LENGTH: 12
<212> TYPE: PRT
<213> ORGANISM: Artificial
<220> FEATURE:
<223> OTHER INFORMATION: Prepared by synthesis

<400> SEQUENCE: 39

Gly Gly Gly Gly Gly Ala Phe Ala Ser Thr Lys Thr
1               5                   10

<210> SEQ ID NO 40
<211> LENGTH: 14
<212> TYPE: PRT
<213> ORGANISM: Artificial
<220> FEATURE:
<223> OTHER INFORMATION: Prepared by synthesis

<400> SEQUENCE: 40

Gly Gly Gly Ala Phe Ala Ser Thr Lys Thr Gly Arg Gly Asp
1               5                   10

<210> SEQ ID NO 41
<211> LENGTH: 16
<212> TYPE: PRT
<213> ORGANISM: Artificial
<220> FEATURE:
<223> OTHER INFORMATION: Prepared by synthesis

<400> SEQUENCE: 41

Gly Gly Gly Pro Phe Ser Ser Thr Lys Thr Gly Ile Lys Val Ala Val
1               5                   10                  15

<210> SEQ ID NO 42
<211> LENGTH: 16
<212> TYPE: PRT
<213> ORGANISM: Artificial
<220> FEATURE:
<223> OTHER INFORMATION: Prepared by synthesis

<400> SEQUENCE: 42

Gly Gly Gly Ala Phe Ala Ser Thr Lys Thr Gly Ile Lys Val Ala Val
1               5                   10                  15

<210> SEQ ID NO 43
<211> LENGTH: 7
<212> TYPE: PRT
<213> ORGANISM: Artificial
```

```
<220> FEATURE:
<223> OTHER INFORMATION: Prepared by synthesis

<400> SEQUENCE: 43

Gly Gly Gly Ala Phe Ala Lys
1               5

<210> SEQ ID NO 44
<211> LENGTH: 11
<212> TYPE: PRT
<213> ORGANISM: Artificial
<220> FEATURE:
<223> OTHER INFORMATION: Prepared by synthesis
<220> FEATURE:
<221> NAME/KEY: PEPTIDE
<222> LOCATION: (3)..(4)
<223> OTHER INFORMATION: GGG

<400> SEQUENCE: 44

Gly Gly Gly Xaa Lys Phe Ser Ser Thr Lys Thr
1               5                   10

<210> SEQ ID NO 45
<211> LENGTH: 17
<212> TYPE: PRT
<213> ORGANISM: Artificial
<220> FEATURE:
<223> OTHER INFORMATION: Prepared by synthesis

<400> SEQUENCE: 45

Phe Gly Gly Gly Ala Phe Ala Ser Thr Lys Thr Gly Ile Lys Val Ala
1               5                   10                  15

Val

<210> SEQ ID NO 46
<211> LENGTH: 11
<212> TYPE: PRT
<213> ORGANISM: Artificial
<220> FEATURE:
<223> OTHER INFORMATION: Prepared by synthesis

<400> SEQUENCE: 46

Tyr Gly Gly Gly Pro Phe Ser Ser Thr Lys Thr
1               5                   10

<210> SEQ ID NO 47
<211> LENGTH: 11
<212> TYPE: PRT
<213> ORGANISM: Artificial
<220> FEATURE:
<223> OTHER INFORMATION: Prepared by synthesis

<400> SEQUENCE: 47

Phe Gly Gly Gly Ala Phe Ser Ser Thr Lys Thr
1               5                   10

<210> SEQ ID NO 48
<211> LENGTH: 7
<212> TYPE: PRT
<213> ORGANISM: Artificial
<220> FEATURE:
<223> OTHER INFORMATION: Prepared by synthesis

<400> SEQUENCE: 48

Pro Phe Ser Ser Thr Lys Thr
1               5
```